US008163976B2

(12) United States Patent
Tien et al.

(10) Patent No.: US 8,163,976 B2
(45) Date of Patent: Apr. 24, 2012

(54) COMPOSITIONS AND METHODS RELATING TO TRANSGENIC PLANTS AND CELLULOSIC ETHANOL PRODUCTION

(75) Inventors: Ming Tien, State College, PA (US); John Carlson, Port Matilda, PA (US); Haiying Liang, Clemson, SC (US)

(73) Assignee: The Penn State Research Foundation, University Park, PA (US)

( * ) Notice: Subject to any disclaimer, the term of this patent is extended or adjusted under 35 U.S.C. 154(b) by 741 days.

(21) Appl. No.: 12/126,569

(22) Filed: May 23, 2008

(65) Prior Publication Data

US 2009/0044292 A1 Feb. 12, 2009

Related U.S. Application Data

(60) Provisional application No. 60/939,726, filed on May 23, 2007.

(51) Int. Cl.
*C12N 15/82* (2006.01)
*C12N 15/10* (2006.01)
*C12N 15/00* (2006.01)

(52) U.S. Cl. ............... 800/278; 800/268; 435/320.1; 435/468; 536/23.1; 536/23.6

(58) Field of Classification Search .................. None
See application file for complete search history.

(56) References Cited

U.S. PATENT DOCUMENTS

| 5,824,842 | A | 10/1998 | MacKay et al. | |
| 5,973,228 | A | 10/1999 | Carlson et al. | |
| 6,066,491 | A * | 5/2000 | Cornelissen et al. | 435/252.3 |
| 6,329,574 | B1 * | 12/2001 | Lundquist et al. | 800/300.1 |
| 6,410,718 | B1 | 6/2002 | Bloksberg et al. | |
| 6,441,272 | B1 | 8/2002 | Ye | |
| 7,071,376 | B2 | 7/2006 | Chapple et al. | |
| 2002/0138878 | A1 | 9/2002 | Sticklen et al. | |
| 2006/0041961 | A1 * | 2/2006 | Abad et al. | 800/289 |
| 2006/0260011 | A1 | 11/2006 | Carter et al. | |

OTHER PUBLICATIONS

Dharmawardhana, D.P. et al., cDNA cloning and heterologous expression of coniferin β-glucosidase, *Plant Molecular Biology*, 40: 365-372, 1999.
Jackson, P.A.P. et al., Rapid Deposition of Extensin during the Elicitation of Grapevine Callus Cultures Is Specifically Catalyzed by a 40-Kilodalton Peroxidase, *Plant Physiology*, 127: 1065-1076, 2001.
Held, M.A. et al., Di-isodityrosine Is the Intermolecular Cross-link of Isodityrosine-rich Extensin Analogs Cross-linked in Vitro, *The Journal of Biological Chemistry*, 279: 55474-55482, 2004.
Keller, B. et al., Glycine-rich cell wall proteins in bean: gene structure and association of the protein with the vascular system, *The EMBO Journal*, 7: 3625-3633, 1988.
Chen, M. et al., Signal Peptide-Dependent Targeting of a Rice α-Amylase and Cargo Proteins to Plastids and Extracellular Compartments of Plant Cells, *Plant Physiology*, 135: 1367-1377, 2004.
Emanuelsson, O. et al., Predicting Subcellular Localization of Proteins Based on their N-terminal Amino Acid Sequence, *Journal of Molecular Biology*, 300: 1005-1016, 2000.
Showalter, A., Structure and Function of Plant Cell Wall Proteins, *The Plant Cell*, 5:9-23, 1993.
Pelegrini, P. et al., Plant γ-thionins: Novel insights on the mechanism of action of a multi-functional class of defense proteins, *The International Journal of Biochemistry and Cell Biology*, 37:2239-2253, 2005.
Bendtsen, J. et al., Improved prediction of signal peptides: SignalP 3.0, *Journal of Molecular Biology*, 340:783-795, 2004.
Cassab, G., Plant Cell Wall Proteins, Annual Review of Plant Physiology and Plant Molecular Biology, 49:281-309, 1998.
Ringli, C. et al., Glycine-rich proteins as structural components of plant cell walls, *Cellular and Molecular Life Sciences*, 58:1430-1441, 2001.
Kuroda, K. et al., Tetramethylammonium Hydroxide (TMAH) Thermochemolysis of Lignin: Behavior of 4-O-Etherified Cinnamyl Alcohols and Aldehydes, *Journal of Agricultural and Food Chemistry*, 53:8859-8865, 2005.
Sluiter, A. et al., Determination of Sugars, Byproducts, and Degradation Products in Liquid Fraction Process Samples, National Renewable Energy Laboratory, Laboratory Analytical Procedure issued Dec. 8, 2006.
Liang, H. et al., A New Approach Toward Lignin Modification: Introducing a Tyrosine Rich Peptide Gene in Hybrid Poplar, *Fourth International Poplar Symposium*, Nanjing, China, Jun. 5-9, 2006.
Sluiter, A. et al., Determination of Structural Carbohydrates and Lignin in Biomass, National Renewable Energy Laboratory, Laboratory Analytical Procedure issued Apr. 25, 2008.
Scholtz, J.M. et al., The Energetics of Ion-Pair and Hydrogen-Bonding Interactions in a Helical Peptide, *Biochemistry*, 32:9668-9676, 1993.
Dowe, N. et al., SSF Experimental Protocols—Lignocellulosic Biomass Hydrolysis and Fermentation, *National Renewable Energy Laboratory*, Laboratory Analytical Procedure issued Oct. 30, 2001.

* cited by examiner

*Primary Examiner* — Brent T Page
(74) *Attorney, Agent, or Firm* — Gifford, Krass, Sprinkle, Anderson & Citkowski, P.C.

(57) ABSTRACT

Transgenic lignocellulosic plants are provided according to embodiments of the present invention, the transgenic plants transformed with an expression cassette encoding a protein operably linked to a signal peptide which targets the protein to a cell wall of the transgenic plant, where at least 5% of the total amino acid residues of the protein are tyrosine, lysine, serine, threonine or cysteine. Methods of increasing lignin-protein bonds in a lignocellulosic plant are provided according to embodiments of the present invention which include expressing a recombinant nucleic acid in a lignocellulosic plant, the recombinant nucleic acid encoding a protein operably linked to a signal peptide which targets the protein to the cell wall of a plant, where at least 5% of the total amino acid residues of the protein are tyrosine, lysine, serine, threonine or cysteine.

10 Claims, 6 Drawing Sheets

US 8,163,976 B2

COMPOSITIONS AND METHODS RELATING TO TRANSGENIC PLANTS AND CELLULOSIC ETHANOL PRODUCTION

REFERENCE TO RELATED APPLICATION

This application claims priority from U.S. Provisional Patent Application Ser. No. 60/939,726, filed May 23, 2007, the entire content of which is incorporated herein by reference.

GOVERNMENT SPONSORSHIP

This invention was made with government support under Contract No. DF-FG02-07ER awarded by the United States Department of Energy's Biosciences Program, Subaward No. 101566 awarded by the United States Department of Transportation, Project No, SC-1700324, technical contribution No. 5459 awarded by the United States Department of Agriculture Cooperative State Research, Education, and Extension Service. The government has certain rights in the invention.

FIELD OF THE INVENTION

The present invention relates generally to transgenic lignocellulosic plants and methods of their use. In specific embodiments the present invention relates to lignocellulosic plants including an expression cassette encoding a protein rich in tyrosine, lysine, serine, threonine or cysteine residues.

BACKGROUND OF THE INVENTION

The limited supply of fossil fuels and the environmental issues associated with their utilization has resulted in much effort put forth to promote renewable resources of energy. Switching to renewable fuels for energy will allow us to become carbon neutral by recycling carbon from plants and reduce carbon from dioxide emissions, which could potentially reduce global warming in future generations and generate new industries with exciting new technologies.

Lignocellulosic plant material is one of the most predominant natural compounds in the biosphere and a common source of feed ingredient for livestock as well as pulp and paper in the wood industry. Lignocellulosic plant material includes cellulose, non-cellulosic polysaccharides and lignin.

Lignin is an insoluble polymer which is a major component of lignocellulosic plants, for instance, constituting between 20-30% of the dry weight of wood. Lignin provides mechanical strength to plants and is primarily responsible for the rigidity of plant stems. Lignin also plays an important role in water transport, chemical resistance and disease resistance in lignocellulosic plants. Lignin is known in the art and is generally described in Hofrichter, M., Lignin, Humic Substances and Coal, Biopolymers, Vol. 1, Wiley-VCH, 2001.

Unfortunately, lignocellulosic material remains largely underutilized due to the difficulty of degrading lignin. For example, production of fermentable sugars is limited because lignin limits hydrolyzability of cellulose. The conversion of lignocellulosic material into ethanol involves hydrolysis of cellulose in the lignocellulosic materials to fermentable sugars, and then fermentation of the sugars to ethanol. Hydrolysis is typically catalyzed by cellulases, and the fermentation is carried out by yeasts or bacteria. Factors that affect the efficiency/cost of lignocellulose hydrolysis include: porosity (accessible surface area), cellulose crystallinity, and lignin content, as described in McMillan, J. D., Pretreatment of Lignocellulosic Biomass, in Enzymatic Conversion of Biomass for Fuels Production. 1994. p. 292-324. Note that each factor impacts accessibility of enzymes to the cellulosic substrate.

Overcoming the lignin barrier is a limiting factor in accessibility of cellulosic substrates, such as cellulose and hemicellulose, to hydrolytic enzymes in biomass conversion. Physical, chemical, and biological processes have been used to pre-treat lignocellulosic materials with the goals of breaking or disrupting the lignin network and/or reducing the crystallinity of cellulose. These processes alter existing structure, providing hydrolytic enzymes increased access to the substrate. Pretreatment is one of the most expensive steps in the conversion of lignocellulosic material to fermentable sugars. Additionally, the overall conversion is poor, due largely to the efficacious nature of lignin in limiting enzymatic access to cellulose and hemicellulose. Thus, facilitation of release of fermentable sugars from lignocellulosic material would be valuable in numerous industrial applications.

Lignin is also a principal impediment to digestibility of lignocellulosic forage crops. Higher lignin content is associated with decreased digestibility in cattle and other herbivores.

Biotechnological efforts to lower lignin content of plants have met with little success since lowered lignin content has been observed to have pleiotropic effects on plant development. These effects include leaf shape and texture, stunted growth, reduced pollen viability, and altered flower morphology, pigmentation, and collapsed vessels, for example as described in Casler, M. D., et al., Genetic Modification of Lignin Concentration Affects Fitness of Perennial Herbaceous Plants., Theor. Appl. Genet., 104:127-131, 2002; and Pedersen, J. F., et al., 2005, Impact of reduced lignin on plant fitness. Crop Sci. 45, 812-819.

Thus, limitations relating to lignin degradation are of central importance in biomass utilization. There is a continuing need for methods and compositions to produce plants characterized by improved processability of plant lignocellulosic materials without undesirable side effects on development and growth of the plants.

SUMMARY OF THE INVENTION

Figure 1:
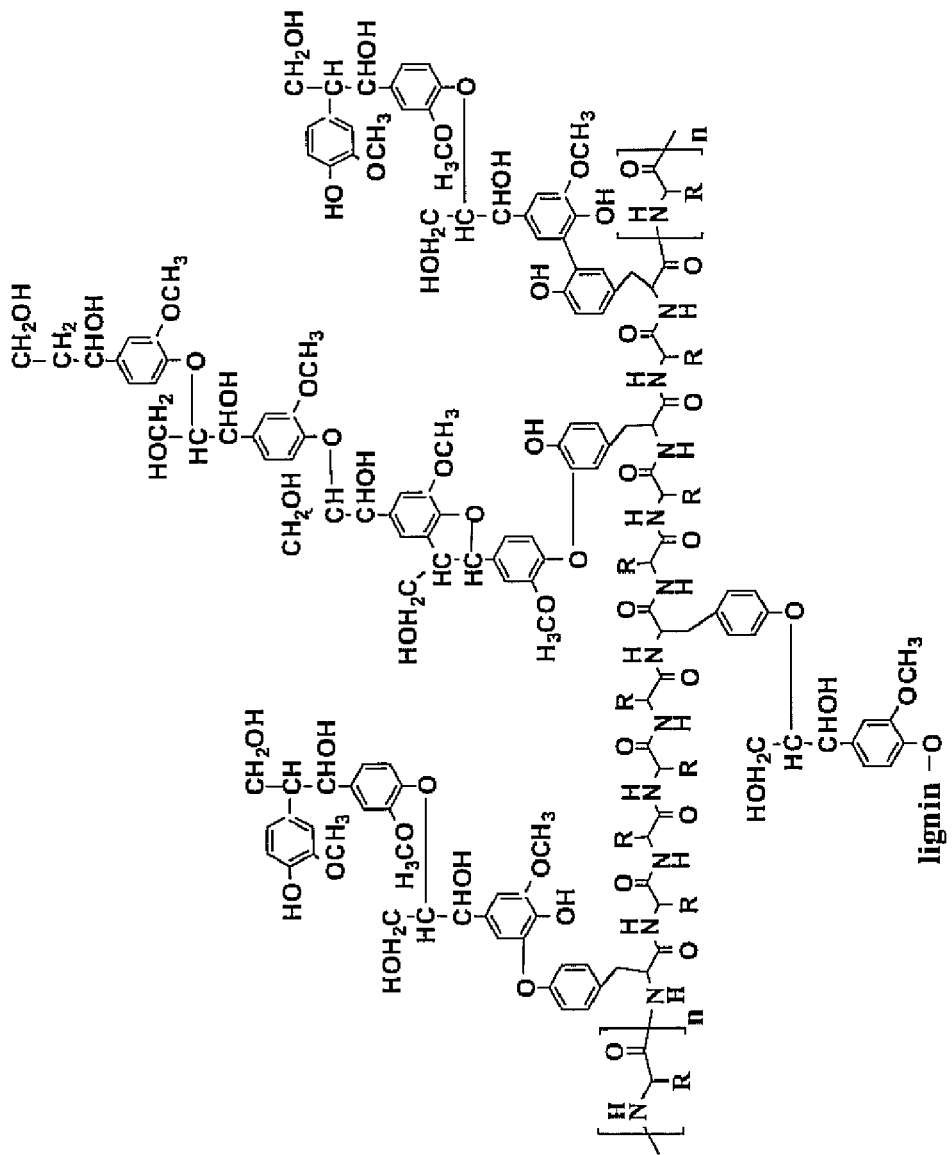
FIG. 1 is a schematic illustrating a modified lignin bonded to a protein rich in tyrosine, lysine, serine, threonine or cysteine residues.

Transgenic lignocellulosic plants are provided according to embodiments of the present invention, the transgenic plants transformed with an expression cassette encoding a protein operably linked to a signal peptide which targets the protein to a cell wall of the transgenic plant, where at least 5% of the total amino acid residues of the protein are tyrosine, lysine, serine, threonine or cysteine. In some embodiments, 6-100%, inclusive, of the total amino acid residues of the protein are tyrosine, lysine, serine, threonine or cysteine. In further embodiments, 10-100%, inclusive, of the total amino acid residues of the protein are tyrosine, lysine, serine, threonine or cysteine. In still further embodiments, 5-100%, inclusive, of the total amino acid residues of the protein are tyrosine.

A transgenic lignocellulosic plant according to embodiments of the present invention is characterized by increased release of fermentable sugars upon treatment of lignocellulosic material of the transgenic lignocellulosic plant with a cellulolytic agent compared to a wild-type plant of the same species.

A transgenic lignocellulosic plant according to embodiments of the present invention is characterized by substantially similar total lignin content compared to a wild-type plant of the same species.

A transgenic lignocellulosic plant according to embodiments of the present invention is characterized by characterized by reduction of lignin content upon treatment of lignocellulosic material of the plant with a peptidolytic agent compared to a wild-type plant of the same species.

A transgenic lignocellulosic plant according to embodiments of the present invention is a transgenic lignocellulosic woody plant.

In particular embodiments, a transgenic plant of the present invention includes an expression cassette encoding a protein selected from the group consisting of: SEQ ID No. 1, SEQ ID No. 3, SEQ ID No. 5, SEQ ID No. 7, a variant of SEQ ID No. 1 rich in tyrosine, lysine, serine, threonine or cysteine, a variant of SEQ ID No. 3 rich in tyrosine, lysine, serine, threonine or cysteine, a variant of SEQ ID No. 5 rich in tyrosine, lysine, serine, threonine or cysteine, a variant of SEQ ID No. 7 rich in tyrosine, lysine, serine, threonine or cysteine, a fragment of SEQ ID No. 1 rich in tyrosine, lysine, serine, threonine or cysteine, a fragment of SEQ ID No. 3 rich in tyrosine, lysine, serine, threonine or cysteine, a fragment of SEQ ID No. 5 rich in tyrosine, lysine, serine, threonine or cysteine, and a fragment of SEQ ID No. 7 rich in tyrosine, lysine, serine, threonine or cysteine.

A method producing fermentable sugar from a lignocellulosic plant is provided according to embodiments of the present invention which includes providing a transgenic plant transformed with an expression cassette encoding a protein and a signal peptide which targets the protein to the cell wall of the transgenic plant, where at least 5% of the total amino acid residues of the protein are tyrosine, lysine, serine, threonine or cysteine; and degrading lignocellulosic material of the plant, yielding fermentable sugar.

In embodiments of methods of the present invention, degrading the lignocellulosic material includes contacting the lignocellulosic material with a cellulolytic agent. Optionally, the cellulolytic agent is a cellulolytic enzyme such as, but not limited to, a cellulase, a hemicellulase, an endoglucanase, a cellulobiohydrolase, a beta-glucosidase, an esterase, a laccase, a peroxidase, and a combination thereof.

In embodiments of methods of the present invention, degrading the lignocellulosic material includes contacting the lignocellulosic material with a peptidolytic agent. In particular embodiments, the peptidolytic agent is a peptidolytic enzyme. Optionally, the peptidolytic agent is an acid.

Methods according to embodiments of the present invention include producing fermentable sugar from a transgenic lignocellulosic plant of the present invention and fermenting the fermentable sugar to yield a fermentation product, such as, but not limited to, ethanol. Optionally, the fermentation of the fermentable sugar is performed substantially simultaneously with degrading lignocellulosic material of the plant.

Methods of increasing lignin-protein bonds in a lignocellulosic plant are provided according to embodiments of the present invention which include expressing a recombinant nucleic acid in a lignocellulosic plant, the recombinant nucleic acid encoding a protein operably linked to a signal peptide which targets the protein to the cell wall of a plant, where at least 5% of the total amino acid residues of the protein are tyrosine, lysine, serine, threonine or cysteine. In a preferred embodiment of a method of increasing lignin-protein bonds in a lignocellulosic plant according to the present invention the recombinant nucleic acid is stably integrated in the genome of the plant.

The lignocellulosic plant expressing the recombinant nucleic acid is characterized by more lignin-protein bonds lignin-protein bonds than a wild-type plant of the same species in embodiments of methods of the present invention.

A method of increasing lignin-protein bonds in a lignocellulosic plant includes expression of the recombinant nucleic acid in a lignifying cell, such as a vascular cell or xylem, in preferred embodiments of the present invention.

An expression cassette is provided according to embodiments of the present invention which includes a nucleic acid encoding a protein operably linked to a signal peptide which targets the protein to a cell wall of the transgenic plant, where at least 5% of the total amino acid residues of the protein are tyrosine, lysine, serine, threonine or cysteine. An expression cassette preferably includes a promoter, such as, but not limited to, a constitutive promoter, an inducible promoter or a cell-type specific promoter.

Embodiments of the present invention provide an expression cassette including a nucleic acid encoding a protein selected from the group consisting of: SEQ ID No. 1, SEQ ID No. 3, SEQ ID No. 5, SEQ ID No. 7, a variant of SEQ ID No. 1 rich in tyrosine, lysine, serine, threonine or cysteine, a variant of SEQ ID No. 3 rich in tyrosine, lysine, threonine or cysteine, a variant of SEQ ID No. 5 rich in tyrosine, lysine, serine, threonine or cysteine, a variant of SEQ ID No. 7 rich in tyrosine, lysine, serine, threonine or cysteine, a fragment of SEQ ID No. 1 rich in tyrosine, lysine, serine, threonine or cysteine, a fragment of SEQ ID No. 3 rich in tyrosine, lysine, serine, threonine or cysteine, a fragment of SEQ ID No. 5 rich in tyrosine, lysine, serine, threonine or cysteine, and a fragment of SEQ ID No. 7 rich in tyrosine, lysine, serine, threonine or cysteine.

Embodiments of the present invention provide an expression cassette including a nucleic acid encoding a protein having the formula [X]n-[ZXXX]m, where X is any amino acid, Z is tyrosine, cysteine, lysine, serine or threonine, where n is an integer in the range of about 0-100, m is an integer in the range of about 5-200, where 5-100%, inclusive, of the total amino acid residues of the protein are tyrosine, cysteine, lysine, serine or threonine residues, and where each [X] and [ZXXX] moiety is disposed independently of each other [X] and [ZXXX] moiety.

Embodiments of the present invention provide an expression cassette including a nucleic acid encoding a protein having the formula NH2-[EXXXK]m-COOH, or NH2-[KXXXE]m-COOH, where m is an integer in the range of about 5-200, where at least one X in each [EXXXK] or [KXXXE] is independently a tyrosine, lysine, serine, threonine or cysteine residue.

Embodiments of the present invention provide an expression cassette including a nucleic acid encoding a protein having the formula NH2-[KAZAE]m-COOH, where each Z is independently a tyrosine, lysine, serine, threonine or cysteine residue, where m is an integer in the range of about 5-200.

A novel non-naturally occurring protein rich in tyrosine, lysine, serine, threonine or cysteine residues is provided according to embodiments of the present invention having the formula [X]n-[ZXXX]m, where X is any amino acid, Z is tyrosine, cysteine, lysine, serine or threonine, where n is an integer in the range of about 0-100, m is an integer in the range of about 5-200, where 5-100%, inclusive, of the total amino acid residues of the protein are tyrosine, cysteine, lysine, serine or threonine residues, and where each [X] and [ZXXX] moiety is disposed independently of each other [X] and [ZXXX] moiety.

A novel non-naturally occurring protein rich in tyrosine, lysine, serine, threonine or cysteine residues is provided according to embodiments of the present invention having the formula: [EXXXK]m-COOH, or NH2-[KXXXE]m-COOH, where m is an integer in the range of about 5-200, where at least one X in each [EXXXK] or [KXXXE] is independently a tyrosine, lysine, serine, threonine or cysteine residue.

A novel non-naturally occurring protein rich in tyrosine, lysine, serine, threonine or cysteine residues is provided according to embodiments of the present invention having the formula: NH2-[KAZAE]m-COOH, where each Z is independently a tyrosine, lysine, serine, threonine or cysteine residue, where m is an integer in the range of about 5-200.

DETAILED DESCRIPTION OF THE INVENTION

Embodiments of the present invention provide methods and compositions for improving processibility of plant lignocellulosic materials. It is a surprising and unexpected finding of the present invention that transgenic plants described herein are characterized by increased release of fermentable sugars upon treatment of lignocellulosic material with a cellulolytic and/or peptidolytic agent compared to a wild-type plant of the same species. The transgenic plants are further characterized by substantially similar total lignin content and substantially similar plant structural characteristics compared to a wild-type plant of the same species.

Methods and compositions of the present invention are useful in processes which utilize plant-derived fermentable sugars, such as production of cellulosic ethanol or other biofuels. Methods and compositions according to the present invention are useful in animal feed, such as cattle feed, to facilitate digestion and improve nutrient recovery. Digestion of lignocellulosic material in transgenic plants of the present invention is facilitated by proteases such as those produced by ruminant microbes, described in Kamande, G. M., et al., J. Dairy Sci. 83, 536-542, 2000.

In particular embodiments, transgenic plants, including, but not limited to transgenic trees, are provided whose secondary cell walls exhibit little or no change in lignin quantity compared to a wild-type plant of the same species, and which are characterized by lignocellulosic material which is more accessible to lignin extraction, such as by treatment with a cellulolytic agent and/or a peptidolytic agent.

Plants and plant cells are provided according to embodiments of the present invention which include an expression cassette encoding a protein and a signal peptide which targets the protein to the cell wall of the transgenic plant, where the protein is rich in tyrosine, lysine, serine, threonine or cysteine.

A protein is "rich" in tyrosine, lysine, serine, threonine or cysteine residues where about 5-100%, inclusive, of the total amino acid residues of the protein are tyrosine, lysine, serine, threonine or cysteine residues. In particular embodiments, a protein is "rich" in tyrosine, lysine, serine, threonine or cysteine where about 6-100%, inclusive, of the total amino acid residues of the protein are tyrosine, lysine, serine, threonine or cysteine residues. In further particular embodiments, a protein is "rich" in tyrosine, lysine, serine, threonine or cysteine where about 7-100%, 8-100%, 9-100%, or 10-100%, inclusive, of the total amino acid residues of the protein are tyrosine, lysine, serine, threonine or cysteine residues.

Embodiments of the present invention are described including an expression cassette encoding a protein rich in tyrosine residues. A protein is "rich" in tyrosine residues where about 5-100%, inclusive, of the total amino acid residues of the protein are tyrosine residues. In particular embodiments, a protein is "rich" in tyrosine where about 6-100%, inclusive, of the total amino acid residues of the protein are tyrosine residues. In further particular embodiments, a protein is "rich" in tyrosine where about 7-100%, 8-100%, 9-100%, or 10-100%, inclusive, of the total amino acid residues of the protein are tyrosine residues.

Embodiments of the present invention are described including an expression cassette encoding a protein rich in two or more of: tyrosine, lysine, serine, threonine and cysteine residues.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Agrobacterium-Mediated Plant Transformation: the Biology behind the "Gene-Jockeying" Tool Microbiology and Molecular Biology Reviews, March 2003, p. 16-37, Vol. 67, No. 1; Maliga, P., Methods in Plant Molecular Biology, Cold Spring Harbor Laboratory Press, New York, 1995; Weissbach, A. and Weissbach, H. Methods for Plant Molecular Biology, Academic Press, 1988; Jackson, J. P. and Linskens, H. F., Genetic Transformation of Plants, Molecular Methods of Plant Analysis, Springer, 2003; and Dashek, W. V., Methods in Plant Biochemistry and Molecular Biology, CRC Press, 1997.

The term "transgenic plant" refers to a plant having one or more, or all, plant cells that contain an expression cassette encoding a protein and a signal peptide which targets the protein to the cell wall of the transgenic plant, where the protein is rich in tyrosine, lysine, serine, threonine or cysteine. In particular embodiments, the expression cassette is stably integrated into the genome. A transgenic plant expresses a protein rich in tyrosine, lysine, serine, threonine or cysteine residues encoded by a nucleic acid of the expression cassette which would not otherwise be expressed in the plant or expresses the encoded protein rich in tyrosine, lysine, serine, threonine or cysteine residues at a different level or in an otherwise different pattern than in a wild-type plant. The term transgenic plant also refers to a transgenic plant part. A transgenic plant of the present invention is a direct transformant, that is, an expression cassette is introduced directly into the plant, or a transgenic plant can be progeny of a direct transformant.

The term "wild-type" is used to refer to a plant or cell which is not modified using a composition or method of the present invention and which therefore does not contain a recombinant expression cassette encoding a protein and a signal peptide which targets the protein to the cell wall of the transgenic plant, where the protein is rich in tyrosine, lysine, serine, threonine or cysteine.

The term "progeny" referring to a transgenic plant describes a transgenic plant of the present invention which is derived from a direct transformant, such as an F1 generation plant. The progeny contains one or more, or all, plant cells having the inherited expression cassette encoding a protein rich in tyrosine, lysine, serine, threonine or cysteine residues. Progeny can have one or more mutations or changes in copy number of the nucleic acid encoding the protein rich in tyrosine, lysine, serine, threonine or cysteine residues which occur by deliberate genetic manipulation or by natural causes. Such mutations and changes are considered to be within the scope of the present invention as long as the protein expressed from the inherited expression cassette is rich in tyrosine, lysine, serine, threonine or cysteine.

The term "protein" refers to a chain of amino acids linked by peptide bonds. The term protein includes oligopeptides having from 2- about 10 peptide bond linked amino acids and polypeptides having about 10 or more peptide bond linked amino acids.

The term "signal peptide" refers to a protein, typically about 3-60 amino acids in length, that directs localization of a second protein to which the signal peptide is operably linked to a particular location within a cell. A "cell wall signal peptide" is a signal peptide that directs localization of a second protein to which the cell wall signal peptide is operably linked to the cell wall of a plant cell.

The terms "nucleic acid" and "nucleic acid sequence" refer to DNA or RNA that is linear or circular, single-stranded or double-stranded.

The term "recombinant nucleic acid" refers to a nucleic acid which is altered, rearranged or modified by genetic engineering methods employed by a human.

The term "expression" refers to transcription of a gene to produce a corresponding mRNA and/or translation of the mRNA to produce the corresponding protein.

The term "expression cassette" refers to a recombinant nucleic acid sequence encoding a protein rich in tyrosine, lysine, serine, threonine or cysteine residues operably linked to a signal peptide which targets the protein to the cell wall of the transgenic plant. The nucleic acid sequence is operably linked to one or more regulatory nucleic acid sequences which facilitates expression of the nucleic acid sequence encoding a protein rich in tyrosine, lysine, serine, threonine or cysteine residues in an appropriate host cell. A promoter is a regulatory nucleic acid sequence preferably included in an expression cassette of the present invention. An expression cassette can be generated recombinantly or synthetically using well-known methodology.

The term "encoding" with respect to a nucleic acid sequence refers to a nucleic acid including the genetic information for translation of the nucleic acid sequence into a specified protein.

An expression cassette can be incorporated into a vector, such as an expression vector and/or cloning vector. The term "vector" refers to a recombinant nucleic acid vehicle for transfer of a nucleic acid. Exemplary vectors are plasmids, cosmids, viruses and bacteriophages. Particular vectors are known in the art and one of skill in the art will recognize an appropriate vector for a specific purpose.

The term "operably linked" refers to a nucleic acid in functional relationship with a second nucleic acid. With respect to proteins, a protein and a signal peptide are operably linked when the linkage effects the localization of the protein to a target location, such as the cell wall of a plant. A regulatory nucleic acid sequence operably linked to a nucleic acid sequence encoding a protein rich in tyrosine, lysine, serine, threonine or cysteine residues facilitates expression of the nucleic acid sequence encoding a protein rich in tyrosine, lysine, serine, threonine or cysteine residues in a host cell when the expression cassette is introduced into the host cell. A regulatory nucleic acid sequence is illustratively a promoter, transfer DNA (T-DNA), an enhancer, a DNA and/or RNA polymerase binding site, a ribosomal binding site, a polyadenylation signal, a transcription start site, a transcription termination site or an internal ribosome entry site (IRES).

A selectable marker is optionally encoded by a nucleic acid in the expression cassette to facilitate the identification and selection of a cell including the expression cassette. Examples of selectable markers include nucleic acid sequences encoding a protein associated with temperature sensitivity, drug resistance, or other phenotypic characteristic. For example, a selectable marker provides the transformed plant cells with resistance to a drug such as, but not limited to, kanamycin, G418, hygromycin, streptomycin, gentamycin, bleomycin, phosphinotricin, sulfionylurea, methotrexate and glyphosate.

A translation leader sequence is optionally included in the expression cassette. A translation leader sequence is a nucleotide sequence positioned between a promoter and a nucleotide sequence encoding a protein rich in tyrosine, lysine, serine, threonine or cysteine residues. A leader sequence has beneficial effects on translation and processing of an RNA molecule. Translation leader sequences are well-known in the art, for example, as described in Nicolaisen M., et al., FEBS Lett., 303(2-3):169-72, 1992; and Turner, R. and Foster, G. D., Mol. Biotechnol. 3:225-236, 1995.

A wide variety of promoters functional in particular host cells are known in the art and one of skill in the art can select a particular promoter for inclusion in an expression cassette and use in facilitating expression of a nucleic acid encoding a protein rich in tyrosine, lysine, serine, threonine or cysteine residues and a signal peptide which targets the protein to the cell wall of a plant in a host cell.

In particular embodiments, a promoter is included in an expression cassette that facilitates expression in a cell of a lignifying tissue, such as, but not limited to, a vascular cell and a xylem cell.

Promoters that can be used include constitutive and inducible promoters as well as promoters that confer cell-type specific expression. Cell-type specific expression refers to both expression exclusively limited to a particular cell type as well as preferential expression in a particular cell type. Exemplary well-known promoters that can be used include, but are not limited to, a dicot promoter; a monocot promoter; a super promoter such as described in Ni, M. et al, Plant J., 7:661-676, 1995; a cauliflower mosaic virus 35S promoter; a cauliflower mosaic virus 19S promoter; an ABA inducible promoter; a plant tissue-specific promoter; an actin promoter; a tomato E8 promoter; a soybean seed protein glycinin promoter; a potato patatin promoter; a ubiquitin promoter; and a light inducible promoter such as ribulose bisphosphate carboxylase small subunit promoter.

In particular embodiments, a promoter conferring lignifying tissue specific or preferred expression is included in an expression cassette. For example, any of various vascular cell- or xylem-specific promoters is included in an expression cassette of the present invention. As a non-limiting example, a hybrid poplar, (P. trichocaix×P. deltoids), PAL2 promoter is included in an expression cassette of the present invention. This promoter and its activity in lignifying tissues is detailed in Gray-Mitsumune, M., et al., 1999, Plant Mol. Biol. 39, 657-669. Further vascular- or xylem-specific promoters that can be included in an expression cassette of the present invention are the Pt4CLIP promoter and others described in Li, L. et al., Proc. Natl. Acad. Sci. USA, 100:4939-4944, 2003, U.S. Pat. No. 7,365,186 and H. Lu et al., Xylem-specific expression of a GRP1.8 promoter::4CL gene construct in transgenic tobacco, J. Plant Growth Regulation, 41(3):279-286, 2003

In preferred embodiments, transgenic plants of the present invention contain an expression cassette encoding the protein rich in tyrosine, lysine, serine, threonine or cysteine residues linked to DNA encoding a cell wall signal peptide. A protein produced by expression of the expression cassette in a host cell contains a signal peptide effective to targets the protein to the cell wall of a host cell. In particular embodiments, the expression cassette encodes a plant protein rich in tyrosine, lysine, serine, threonine or cysteine residues which is a plant cell wall protein and a signal peptide which targets the protein to the cell wall of a transgenic plant cell containing the expression cassette. A polynucleotide encoding the signal peptide can encode the signal peptide naturally associated with the plant cell wall protein, or, can optionally encode a heterogeneous signal peptide.

In further embodiments, the expression cassette encodes a plant protein rich in tyrosine, lysine, serine, threonine or cysteine residues which is a non-naturally occurring protein. A polynucleotide encoding a naturally occurring or a non-naturally occurring signal peptide can be operably linked to the polynucleotide encoding the non-naturally occurring protein rich in tyrosine, lysine, serine, threonine or cysteine residues to target the protein to the cell wall of a plant cell containing the expression cassette.

A nucleic acid encoding a signal peptide is inserted into an expression cassette using well-known methods, particularly recombinant nucleic acid technology, to encode a protein rich in tyrosine, lysine, serine, threonine or cysteine residues operably linked to the signal peptide.

In particular embodiments, a nucleic acid encoding the signal peptide from beta-glucosidase from *Pinus contorta*, MEVSVLMWVLLFYSLLGFQVTTA, identified herein as SEQ ID No. 13, is linked to a polynucleotide encoding a protein rich in tyrosine, lysine, serine, threonine or cysteine residues in an expression cassette of the present invention. SEQ ID NO. 16 is an example of a nucleic acid encoding the signal peptide from beta-glucosidase from *Pinus contorta*. Further examples of signal peptides that can be used to target a protein rich in tyrosine, lysine, serine, threonine or cysteine residues to the cell wall of the transgenic plant include MATIHRLPSLVFLVLLALGVCSARRALLTL, identified herein as SEQ ID No. 14, or MATSKVLLSNVLFVFVCFGICSAARTLLTL, identified herein as SEQ ID No. 15.

Further signal peptides operative to target a protein to the cell wall of the transgenic plant and which can be encoded by a polynucleotide in an expression cassette of the present invention are known in the art or can be identified using well-known methodology, for example as described in Emanuelsson, O. et al., J. Mol. Biol., 300:1005-1016, 2000.

Transferred DNA (T-DNA) is a genetic element of the tumor inducing (Ti) plasmid of bacteria such as *Agrobacterium tumefaciens* and *Agrobacterium rhizogenes* well-known as capable of integrating a nucleic acid sequence contained between a left border sequence of a T-DNA and a right border sequence of a T-DNA into a plant genome.

In particular embodiments, methods of the present invention include plant modification by introducing a protein rich in tyrosine, lysine, serine, threonine or cysteine residues into the cell walls of lignifying plant tissues via genetic transformation.

In particular embodiments, genetic transformation of a plant is used to introduce a protein rich in tyrosine, lysine, serine, threonine or cysteine residues into the cell walls of lignifying plant tissues and the tyrosine, lysine, serine, threonine or cysteine residues provide reactive sites for bonding with lignin and/or lignin precursors.

Transgenic plants of the present invention are provided which express 1) an increased an amount of a protein rich in tyrosine, lysine, serine, threonine or cysteine residues typically present in the cell wall of a wild-type plant and/or 2) a protein rich in tyrosine, lysine, serine, threonine or cysteine residues which is foreign to the plant.

An expression cassette encoding a protein rich in tyrosine, lysine, serine, threonine or cysteine residues according to embodiments of the present invention is used to transform a host. The term "transformation" refers to a process of introducing a recombinant nucleic acid into a recipient host. The host can be a plant cell; including a plant cell in vitro, a plant cell in a plant, i.e. in planta, a plant cell in a plant part. The term "plant part" refers to any portion of a plant, including, but not limited to, seeds, stems, embryos, pollen, leaves, tubers, protoplasts, calli, roots, stamens, ovules, meristematic regions, gametophytes, sporophytes and microspores.

Methods of transformation well-known in the art include methods for transformation of angiosperms including dicots and monocots; and gymnosperms; among others. Any method of transformation can be used and well-known plant transformation techniques include, but are not limited to, *Agrobacterium*-mediated transformation, electroporation, particle accelerated transformation also known as "gene gun" technology, liposome-mediated transformation, microinjection, polyethylene glycol mediated transformation, heat shock mediated transformation and virus-mediated transformation. Examples of methods of transformation are described in *Agrobacterium*-Mediated Plant Transformation: the Biology behind the "Gene-Jockeying" Tool: Microbiology and Molecular Biology Reviews, March 2003, p. 16-37, Vol. 67, No. 1; Maliga, P., Methods in Plant Molecular Biology, Cold Spring Harbor Laboratory Press, New York, 1995; Weissbach, A. and Weissbach, H. Methods for Plant Molecular Biology, Academic Press, 1988; Jackson, J. F. and Linskens, H. F., Genetic Transformation of Plants, Molecular Methods of Plant Analysis, Springer, 2003; and Dashek, W. V., Methods in Plant Biochemistry and Molecular Biology, CRC Press, 1997.

The development, regeneration and cultivation of plants containing a recombinant nucleic acid from a cell, plant part and/or plant transformed with the recombinant nucleic acid is well-known in the art as exemplified in *Agrobacterium*-Mediated Plant Transformation: the Biology behind the "Gene- Jockeying" Tool: Microbiology and Molecular Biology Reviews, March 2003, p. 16-37, Vol. 67, No. 1; Maliga, P., Methods in Plant Molecular Biology, Cold Spring Harbor Laboratory Press, New York, 1995; Weissbach, A. and Weissbach, H. Methods for Plant Molecular Biology, Academic Press, 1988; Jackson, J. F. and Linskens, H. F., Genetic Transformation of Plants, Molecular Methods of Plant Analysis, Springer, 2003; and Dashek, W. V., Methods in Plant Biochemistry and Molecular Biology, CRC Press, 1997.

In general, transformed cells, embryos or seeds are selected and cultured to produce rooted transgenic plantlets which can then be planted in soil or another suitable plant growth medium.

One of skill in the art will recognize that individual transformation events will result in different levels of expression of a transgene, as well as different patterns of expression, such as temporal or spatial patterns, in a cell or organism. Routine screening of multiple transformation events is performed to obtain lines having a desired level of expression of the transgene and/or a desired pattern of expression. Such routine screening is accomplished using well-known techniques such as Southern blot, Northern blot, Western blot and/or phenotypic analysis for a desired characteristic.

Development and regeneration of transformed plants is well-known in the art. Regenerated transgenic plants are preferably self-pollinated to produce homozygous transgenic plants. Optionally, a regenerated transgenic plant is pollinated by a plant which is not a transgenic plant of the present invention, or, pollen from a regenerated transgenic plant is used to pollinate a plant which is not a transgenic plant of the present invention. Development and regeneration of transgenic plants from a transformed plant part are also well-known in the art.

Methods and compositions of the present invention are not limited to particular lignocellulosic plants. In any transformable lignocellulosic crop plant or lignocellulosic tree used for animal feed or biofuel in which lignin content is a problem, the methods and compositions for expressing a protein rich in tyrosine, lysine, serine, threonine or cysteine residues in a plant as described herein can be used to improve the transformable crop plant or tree, for instance for use as biofuel or animal feed. Non-limiting examples include poplar trees, Eucalyptus trees, loblolly pine (*Pinus taeda*) and radiata pine (*Pinus radiata*) trees, spruce trees, alfalfa and maize.

In preferred embodiments, a plant transformed to provide a transgenic plant according to the present invention is a lignocellulosic plant, that is, a plant which contains lignocellulose. Lignocellulosic plants include woody and non-woody plants. Lignocellulosic plants are well-known and a plant can be identified as lignocellulosic by any of various assays, such as the Klason method of plant material analysis and/or staining of plant sections or cells with phloroglucinol-HCl or potassium permanganate.

Transgenic lignocellulosic plants according to embodiments of the present invention include transgenic monocots and transgenic dicots. The term "monocot" refers to monocotyledonous plant, that is, a type of plant whose embryos have one cotyledon or seed leaf. Transgenic lignocellulosic monocots according to embodiments of the present invention include, but are not limited to, plants of the family Arecaceae; Orchidaceae; Dioscoreaceae; Liliaceae; Musaceae; and Poaceae, such as corn, wheat, oats, rice, barley as well as other cereal grasses. Transgenic lignocellulosic dicots according to embodiments of the present invention include, but are not limited to, plants of the family Anacardiaceae; Asteraceae; Brassicaceae; Cactaceae; Cucurbitaceae; Euphorbiaceae; Fabaceae; Linaceae; Malvaceae; Oleaceae; Rosaceac; Rubiaceae; Rutaceae; Solanaceae; Theaceae; and Vitaceae.

Transgenic lignocellulosic trees according to embodiments of the present invention include, but are not limited to, plants of the family Betulaceae; Casuarinaceae; Fagaceae; Juglandaceae; Sapindaceae; lippocastanaceae; Rutaceae; Meliaceae; Simaroubaceae; Anacardiaceae; and Cornaceae.

Transgenic lignocellulosic Gymnosperms according to embodiments of the present invention include, but are not limited to, transgenic plants of the family Cupressaceae; Taxaceae; Taxodiaceae; and Pinaceae.

In particular embodiments of the present invention, a transgenic plant is a transgenic woody plant. The term "woody plant" refers to a vascular plant having a stem characterized by a layer of bark. Transgenic lignocellulosic woody plants according to embodiments of the present invention include, but are not limited to, woody plants of the family Betulaceae; Casuarinaceae; Fagaceae; Juglandaceae; Sapindaceae; Hippocastanaceae; Rutaceae; Meliaceae; Simaroubaceae; Anacardiaceae; and Cornaceae.

In a particular example, methods and compositions of the present invention for making and using a transgenic plant expressing a recombinant nucleic acid encoding a protein rich in tyrosine, lysine, serine, threonine or cysteine residues are applicable to poplar trees. Poplars trees can grow on marginal land and can be harvested every three to five years, yet regrow quicker because the extensive root system of these trees survives. Unfortunately, the poplar biomass is in the form of lignocellulose and lignin interferes both with the production of paper and ethanol from these trees. The hybrid poplar line, *Populus×euramericana* ('Ogy'), is characterized by a transformation rate that is fairly high (6.6%). *Agrobacterium*-mediated transformation and regeneration of poplar are achieved, for instance, according to the protocol described herein and as detailed in Liang, H. Y. et al., 2001, Plant Mol. Biol. 45, 619-629.

Eucalyptus trees are grown extensively in plantations in tropical and sub-tropical locations for wood, fiber and biomass. Eucalyptus grows very quickly and accumulates a great amount of biomass over relatively short rotations. Like hybrid poplar, however, the biomass is in the form of lignocellulose in which the lignin interferes both with the production of paper and ethanol. Eucalyptus is readily transformable via *Agrobacterium* (e.g., Mullins et al. (1997) Plant Cell Reports 16: 787-791). Thus, methods and compositions of the present invention for making and using a transgenic plant expressing a recombinant nucleic acid encoding a protein rich in tyrosine, lysine, serine, threonine or cysteine residues are applicable to and will have the same benefits in the eucalypts as in poplars.

Loblolly pine (*Pinus radiata*) and radiata pine (*Pinus radiata*) trees are also grown extensively in plantations for wood, fiber and biomass, although in temperate climates. Pine plantations could supply large amounts of energy in many areas. However the lignin in such woody biomass interferes with liquid fuel production. Thus, methods and compositions of the present invention for making and using a transgenic plant expressing a recombinant nucleic acid encoding a protein rich in tyrosine, lysine, serine, threonine or cysteine residues are applicable to and will have the same benefits in pines as in poplars.

Spruce trees are planted across large areas in northern climates for wood, fiber and biomass. Like other trees, however, the lignin in spruce woody will interfere with liquid biofuels production. Thus, methods and compositions of the present invention for making and using a transgenic plant expressing a recombinant nucleic acid encoding a protein rich in tyrosine, lysine, serine, threonine or cysteine residues are applicable to and will have the same benefits in spruce as in poplars.

Alfalfa is an important feedstock for livestock, which grows well in N-limited soils. However too much alfalfa in the diet causes severe indigestion problems with ruminants because of its high lignin content. High lignin content in alfalfa will also limit its use as a feedstock for liquid fuel production. Thus, methods and compositions of the present invention for making and using a transgenic plant expressing a recombinant nucleic acid encoding a protein rich in tyrosine, lysine, serine, threonine or cysteine residues are applicable to and will have the same benefits in alfalfa to improve the digestibility and break down of alfalfa lignocellulosic material through increased peptide-lignin chemical bonds which are accessible to protease and cellulase digestive enzymes as in poplars.

The utility of maize stover (cobs, stems and leaves) for biofuel production is limited by lignin content. Thus, methods and compositions of the present invention for making and using a transgenic plant expressing a recombinant nucleic acid encoding a protein rich in tyrosine, lysine, serine, threonine or cysteine residues are applicable to and will have the same benefits in maize as in poplars.

Transgenic plants of the present invention are not limited with regard to a specific recombinant protein rich in tyrosine, lysine, serine, threonine or cysteine residues expressed therein.

Examples of plant cell wall proteins rich in tyrosine, lysine, serine, threonine or cysteine residues which are recombinantly expressed in a transgenic plant of the present invention include, but are not limited to, extensins, Glycine-rich Proteins, Proline-rich Proteins and thionins, for instance as described in Pelegrini, B. Et al., Int. J. Biochem. Cell. Biol., 37:2239-2253; Showalter, A. M., Plant Cell, 5:9-23, 1993; Bunge, S., et al., Mol. Gen. Genet. 231 (3), 460-468, 1992; and Wu, H. M., et al., Proc. Natl. Acad. Sci. U.S.A., 90(14): 6829-6833, 1993.

An example of a tyrosine rich protein recombinantly expressed in a transgenic plant of the present invention is "tyrosine-rich hydroxyproline-rich glycoprotein" from *Petroselinum crispum* (parsley). The amino acid sequence of this protein including the signal peptide from beta-glucosidase from *Pinus contorta* is included herein as SEQ ID No.1. The encoded protein is characterized in that 11.7% of the total amino acid residues of the protein of SEQ ID No.1 are tyrosine residues. A DNA sequence encoding "tyrosine-rich hydroxyproline-rich glycoprotein" from *Petroselinum crispum* operably linked to the signal peptide from beta-glucosidase from *Pinus contorta* is included herein as SEQ ID No.2.

A further example of a tyrosine rich protein recombinantly expressed in a transgenic plant of the present invention is a plant "glycine-rich protein" (GRP). Glycine-rich proteins are found in the cell walls of many plant species as described in Mousavi, A. and Hotta, Y., Appl. Biochem. Biotechnol. 120: 169-174, 2005; Ringli, C. et al., Cell Mol. Life. Sci., 58:1430-1431, 2001; and Sachetto-Martins, G. et al., Biochim. Biophys. Acta, 1492:1-14, 2000. Examples of these are two forms of the GRP in beans, a GRP1.8 and a GRP1.0, detailed in Keller, B., et al., 1989, Proc. Natl. Acad. Sci. USA. 86:1529-1533; and Keller, B., et al., 1989, EMBO J. 8:1309-1314. Both contain an amino terminal signal peptide of approximately 30 amino acids. In addition to the high glycine content, GRPs also contain a high content of tyrosine (Tyr) residues. The GRP1.8 protein contains 34 tyrosine residues out of a total of 465 total amino acids, about 7% of the total amino acids. The GRP1.0 protein has slightly fewer Tyr residues, at 5% tyrosine.

The amino acid sequence of GRP1.8 protein found in cell walls of beans has the amino acid sequence shown as SEQ ID NO. 3. A DNA sequence encoding GRP1.8 protein is included herein as SEQ ID No. 4.

The amino acid sequence of GRP1.0 protein found in cell walls of beans has the amino acid sequence shown as SEQ ID NO. 5. A DNA sequence encoding GRP1.0 protein is included herein as SEQ ID No. 6.

In particular embodiments of the present invention, an expression cassette includes a nucleic acid sequence encoding the protein of SEQ ID Nos. 1, 3, 5, a variant thereof, or a tyrosine-rich fragment thereof.

A "fragment" of a protein described herein is truncated relative to the full-length protein disclosed. A fragment of a protein encoded by an expression cassette of the present invention includes at least 2 amino acids and is a protein rich in tyrosine, lysine, serine, threonine or cysteine residues.

In particular embodiments of the present invention, an expression cassette includes nucleic acid sequence SEQ ID Nos. 2, 4, 6, a variant thereof, or a fragment of SEQ ID Nos. 2, 4, or 6 encoding a tyrosine-rich protein. It is appreciated that, due to the degeneracy of the genetic code, a protein can be encoded by more than one nucleic acid sequence. Thus, an expression cassette can include a nucleic acid sequence having one or more "silent" changes, that is, differences in the nucleic acid sequence compared to SEQ ID Nos. 2, 4 or 6 which encode the protein of SEQ ID Nos. 1, 3, or 5, respectively.

As noted herein, a protein encoded by an expression cassette in a transgenic plant of the present invention is "rich" in tyrosine, lysine, serine, threonine or cysteine residues. Thus, variants of the nucleic acid sequences of SEQ ID Nos. 2, 4, 6 which encode a protein having as little as about 10% amino acid sequence identity with the proteins of SEQ ID Nos. 1, 3, or 5 can be included in an expression cassette in a transgenic plant of the present invention as long as the nucleic acid sequence encodes a protein rich in tyrosine, lysine, serine, threonine or cysteine residues.

Percent identity is determined by comparison of amino acid or nucleic acid sequences. For instance, a reference sequence and a putative variant amino acid or nucleic acid sequence are compared. Algorithms used for determination of percent identity illustratively include the algorithms of S. Karlin and S. Altshul, PNAS, 90:5873-5877, 1993; T. Smith and M. Waterman, Adv. Appl. Math. 2:482-489, 1981, S, Needleman and C. Wunsch, J. Mol. Biol., 48:443-453, 1970, W. Pearson and D. Lipman, PNAS, 85:2444-2448, 1988 and others incorporated into computerized implementations such as, but not limited to, GAP, BESTFIT, FASTA, TFASTA; and BLAST, for example incorporated in the Wisconsin Genetics Software Package, Genetics Computer Group, 575 Science Drive, Madison, Wis.) and publicly available from the National Center for Biotechnology Information.

The term "variant" refers to a protein characterized by an amino acid sequence having a specified "percent identity" to the amino acid sequence of a tyrosine, lysine, serine, threonine or cysteine rich protein disclosed herein and which is itself a protein rich in tyrosine, lysine, serine, threonine or cysteine residues.

In particular embodiments, a variant of a protein rich in protein rich in tyrosine, lysine, serine, threonine or cysteine residues disclosed herein has at least 70%, at least 75%, or at least 85%, 90%, 91%, 92%, 93%, 94%, 95%, 96%, 97%, 98%, 99%, or greater, amino acid sequence identity to the protein rich in protein rich in tyrosine, lysine, serine, threonine or cysteine residues and is itself a protein rich in tyrosine, lysine, serine, threonine or cysteine residues.

In further embodiments, a variant of SEQ ID No. 1, 3 or 5 has at least 70%, at least 75%, or at least 85%, 90%, 91%, 92%, 93%, 94%, 95%, 96%, 97%, 98%, 99%, or greater, amino acid sequence identity to SEQ ID No. 1, 3 or 5 and is itself a protein rich in tyrosine, lysine, serine, threonine or cysteine residues.

A variant protein is encoded by a nucleic acid sequence readily discernable by one of skill in the art. In particular embodiments, a variant protein is encoded by a nucleic acid sequence having substantial identity to SEQ ID No. 2, 4 or 6.

In particular embodiments, a nucleic acid sequence having substantial identity to SEQ ID No. 2, 4 or 6 has at least 70%, at least 75%, or at least 85%, 90%, 91%, 92%, 93%, 94%, 95%, 96%, 97%, 98%, 99%, or greater, nucleic acid sequence identity to SEQ ID No. 2, 4 or 6 and encodes a protein rich in tyrosine, lysine, serine, threonine or cysteine residues.

In particular embodiments, a nucleic acid sequence having substantial identity with SEQ ID No. 2, 4 or 6 is characterized as having a complementary nucleic acid sequence capable of hybridizing to SEQ ID No. 2, 4 or 6 under stringent hybridization conditions.

The terms "hybridizing" and "hybridization" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. High stringency hybridization conditions are those which only allow hybridization of substantially complementary nucleic acids. Determination of stringent hybridization conditions is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002.

High stringency hybridization conditions are known in the art. For instance, high stringency conditions can be achieved by incubating the nucleic acids overnight (e.g., at least 12 hours) in a hybridization solution containing, e.g., about 5×SSC, 0.5% SDS, 100 μg/ml denatured salmon sperm DNA and 50% formamide, at 42° C. High stringency conditions can be designed that allow, e.g., for less than 5% bp mismatch, for example, washing the hybridized nucleic acids twice in 0.1% SSC and 0.1% SDS for 30 min at 65° degree.

Other non-limiting examples of high stringency conditions include a final wash at 65° C. in aqueous buffer containing 30 mM NaCl and 0.5% SDS. Another example of high stringency conditions include hybridization in 7% SDS, 0.5 M NaPO4, pH 7, 1 nM EDTA at 50° C., e.g., overnight, followed by one or more washes with a 1% SDS solution at 42° C.

Novel proteins rich in tyrosine, lysine, serine, threonine or cysteine residues are provided according to embodiments of the present invention. Such proteins are generated by well-known chemical synthetic or recombinant techniques given the teachings herein and the knowledge in the art.

In embodiments of the present invention, a protein rich in tyrosine, lysine, serine, threonine or cysteine residues includes YXXX, SXXX, KXXX, TXXX and/or CXXX repeats, where Y is a symbol representing a tyrosine residue, S is a symbol representing a serine residue, K is a symbol representing a lysine residue, T is a symbol representing a threonine residue, C is a symbol representing a cysteine residue and each X is independently any amino acid residue. A general formula for such a protein is $NH_2$-$[X]_n$-$[ZXXX]_m$-COOH, where each Z is independently Y, S, K, R or C, where n is an integer in the range of about 0-100, m is an integer in the range of about 5-200, where m is at least 5, at least 10, or at least 20, and where about 5-100%, inclusive, of the total amino acid residues of the protein are tyrosine, lysine, serine, threonine or cysteine residues. Each $[X]_n$ and each $[ZXXX]_m$, is optionally disposed in any order with respect to each other in particular embodiments.

An example of a protein having the general formula $NH_2$-$[X]_n$-$[ZXXX]_m$-COOH, where each Z is independently Y, S, K, R or C, where n is an integer in the range of about 0-100, m is an integer in the range of about 5-200, is disclosed herein as SEQ ID No. 7. The protein of SEQ ID No. 7 has the formula $NH_2$-$[X]_4$-$[YXXX]_{22}$-COOH. The protein of SEQ ID No. 7 is encoded by the DNA sequence having SEQ ID No. 8. A DNA sequence encoding a signal peptide which targets the protein to the cell wall of the transgenic plant is linked to the DNA sequence of SEQ ID No. 8., for instance using recombinant nucleic acid technology well-known to the skilled artisan.

In embodiments of the present invention, an expression cassette for transformation of a lignocellulosic plant encodes the protein of SEQ ID No. 7, a variant thereof, or a fragment thereof rich in tyrosine, lysine, serine, threonine or cysteine residues. In certain embodiments of the present invention, an expression cassette includes nucleic acid sequence SEQ ID No. 8, a variant thereof or a fragment of SEQ ID No. 8 encoding a protein rich in tyrosine, lysine, serine, threonine or cysteine residues.

In embodiments of the present invention, a variant of SEQ ID No. 7 has at least 70%, at least 75%, or at least 85%, 90%, 91%, 92%, 93%, 94%, 95%, 96%, 97%, 98%, 99%, or greater, amino acid sequence identity to SEQ ID No. 7 and is itself a protein rich in tyrosine, lysine, serine, threonine or cysteine residues.

A nucleic acid sequence having substantial identity to SEQ ID No. 8 has at least 70%, at least 75%, or at least 85%, 90%, 91%, 92%, 93%, 94%, 95%, 96%, 97%, 98%, 99%, or greater, nucleic acid sequence identity to SEQ ID No. 8 and encodes a protein rich in tyrosine, lysine, serine, threonine or cysteine residues in embodiments of the present invention.

In embodiments of the present invention, a substantially identical nucleic acid sequence is characterized as having a complementary nucleic acid sequence capable of hybridizing to a nucleic acid sequence encoding SEQ ID No. 8 under stringent hybridization conditions.

In embodiments of the present invention, a protein rich in tyrosine, lysine, serine, threonine or cysteine residues is also rich in a helix-forming amino acid, such as alanine. One embodiment includes tyrosines randomly positioned among other amino acids in a helix-forming protein structure. In a further embodiment, a protein of the present invention includes only tyrosine and alanine residues, with the tyrosine residues spaced apart so that 10 alanine residues separate each two tyrosines.

A protein rich in tyrosine, lysine, serine, threonine or cysteine residues according to embodiments of the present invention, is characterized by hydrogen bonding of the amino acid side chains to stabilize helix formation of the protein. An exemplary protein peptide including hydrogen bonding of the amino acid side chains stabilizing helix formation has Glu and Lys residues characterized by i and i+4 spacing in the protein to stabilize helix formation as described in Scholtz, J. M., et al., 1993, Biochemistry. 32, 9668-9676. General formulas for stabilized helix-forming proteins rich in tyrosine, lysine, serine, threonine or cysteine residues according to embodiments of the present invention are $NH_2$-$[EXXXK]_m$-COOH, and $NH_2$-$[KXXXE]_m$-COOH, where m is an integer in the range of about 5-200, where at least one X in each [EXXXK] or [KXXXE] is independently a tyrosine, lysine, serine, threonine or cysteine residue.

In particular embodiments, a stabilized helix-forming protein rich in tyrosine, lysine, serine, threonine or cysteine residues has the formula $NH_2$-$[KAZAE]_m$-COOH, where each Z is independently a tyrosine, lysine, serine, threonine or cysteine residue, where m is an integer in the range of about 5-200.

In particular embodiments, a protein rich in tyrosine, lysine, serine, threonine or cysteine residues has a molecular weight of about 5 kD.

Modified Lignin

Particular embodiments of methods and compositions of the present invention provide transgenic plants including modified lignin, that is, lignin chemically bonded to proteins rich in tyrosine, lysine, serine, threonine or cysteine residues.

The structure of lignin is heterogeneous and is formed by polymerization of monolignols which are typically p-hydroxycinnamyl alcohols. The three most abundant p-hydroxycinnamyl alcohols are para-coumaryl alcohol, coniferyl alcohol and sinapyl alcohol.

In particular embodiments, a transgene encoded protein rich in tyrosine, threonine or cysteine residues is bonded by free radical coupling with lignin and/or a p-hydroxycinnamyl alcohol precursor of lignin.

Without wishing to be bound by theory, it is believed that a protein rich in tyrosine, serine and/or threonine encoded by an expression cassette in a transgenic plant of the present invention reacts with lignin and/or a monolignol by a free radical coupling mechanism to produce lignin bound to the protein. A schematic reaction is illustrated in Scheme 1 which shows a monolignol and a tyrosine residue of a protein reacting to form three types of products: two stereoisomers of the monolignol and the tyrosine residue of the protein bonded through an ether linkage; and a dityrosine residue linking a protein and lignin. Each R1 in Scheme 1 represents an amino acid residue of the protein bonded to lignin.

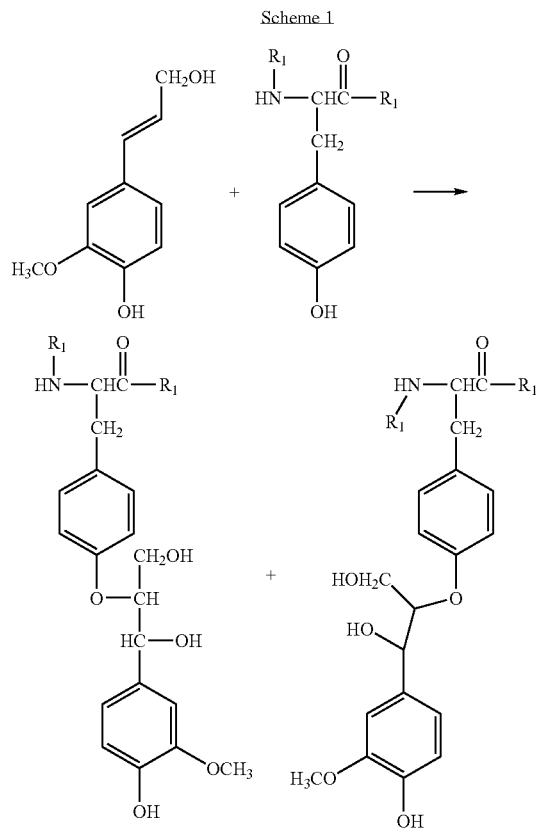

Scheme 1

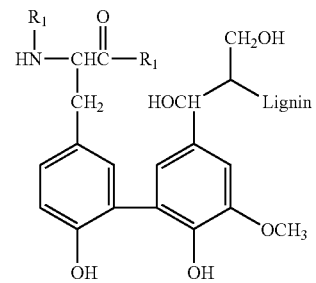

Without wishing to be bound by theory, it is believed that a protein rich in tyrosine, lysine and/or cysteine encoded by an expression cassette in a transgenic plant of the present invention reacts with a quinone moiety of lignin by a Michael addition mechanism to produce lignin bound to the protein.

A schematic reaction is illustrated in Scheme 2 which shows a quinone moiety of lignin and a cysteine residue (top) of a protein and a lysine residue (bottom) of a protein reacting to form two types of products: lignin and the cysteine residue of the protein bonded through a thioether linkage; and the lysine residue of the protein bonded through a secondary amine linkage. Each R1 in Scheme 2 represents an amino acid residue of the protein bonded to lignin.

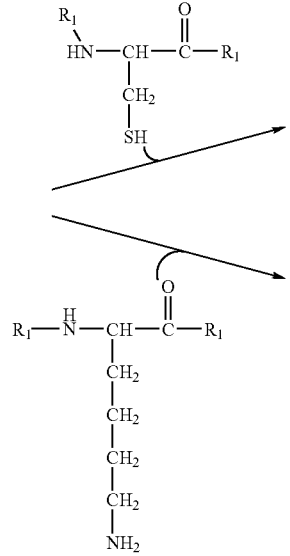

Scheme 2

-continued

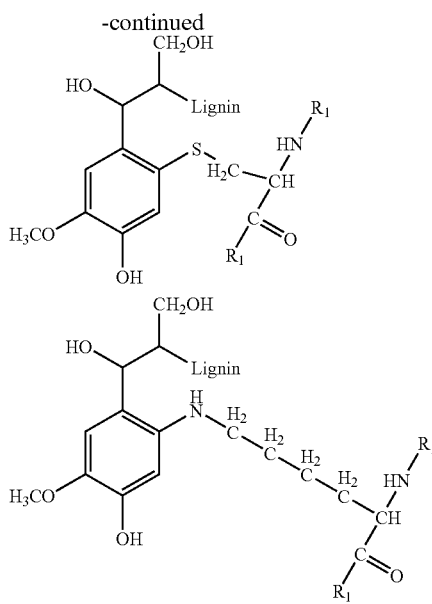

Products of coupling of the transgene encoded protein rich in tyrosine, lysine, serine, threonine or cysteine residues and lignin and/or a p-hydroxycinnamyl alcohol precursor of lignin endogenous to the transgenic plant result in modified lignin in a transgenic plant according to embodiments of the present invention. The bonding of lignin and the expression cassette encoded protein rich in tyrosine, lysine, serine, threonine or cysteine residues is believed to result in suppression of intermolecular bonds within the lignin polymer structure, for instance, by replacement of at least a portion of lignin-lignin linkages with linkages between lignin and tyrosine, lysine, serine, threonine or cysteine residues of the expression cassette encoded protein rich in tyrosine, lysine, serine, threonine or cysteine residues.

An example of a modified lignin structure is shown in FIG. 1 illustrating a tyrosine rich protein bonded to lignin. Each R in FIG. 1 represents an amino acid side chain of the protein. The symbol "n" refers to an integer and indicates a number of amino acid residues.

Detection of modified lignin in a transgenic plant of the present invention is accomplished using any of various well-known techniques, illustratively including NMR spectroscopy, tetramethylammonium hydroxide (TMAH) thermochemolysis, and Dynamic Mechanical Analyses of the transgenic plant lignin.

Methods and compositions according to embodiments of the present invention improve accessibility of cellulolytic enzymes to cellulose in the cell walls, for instance through increasing the number of protein-lignin cross links in lignocellulosic material in a plant.

Transgenic plants according to embodiments of the present invention are characterized by lignin chemically bonded to proteins rich in tyrosine, lysine, serine, threonine or cysteine residues which facilitate removal of lignin using a peptidolytic agent and increase release of fermentable sugar using a cellulolytic and/or peptidolytic agent. Digestion of the protein to which the lignin is bound in the transgenic plants "crack" the lignin. Replacing even a small fraction of lignin-lignin linkages with protein-lignin linkages facilitates the "cracking" of lignin such that the cellulosic components are more easily hydrolyzed.

Methods of increasing lignin-peptide bonds in a lignocellulosic plant are provided according to embodiments of the present invention which include transforming a plant cell with an expression cassette encoding a protein and a signal peptide which targets the protein to the cell wall of the plant cell, where at least 5% of the total amino acid residues of the protein are tyrosine, lysine, serine, threonine or cysteine. The host plant cell is, for example, an isolated cell, a cell of a plant or plant part and the host cell, plant part or plant is developed and/or regenerated to produce a transgenic plant expressing a protein operably linked to a signal peptide which targets the protein to the cell wall of the plant cell, where at least 5% of the total amino acid residues of the protein are tyrosine, lysine, serine, threonine or cysteine. The resulting transgenic plants are characterized by an increased amount of protein-lignin bonds due to lignin covalently bonded to the expressed protein rich in tyrosine, lysine, serine, threonine or cysteine residues.

Analysis of Transgenic Plant Structural Characteristics

In preferred embodiments, transgenic plants according to the present invention are characterized by substantially similar structural integrity compared to a wild-type plant. The structural integrity of a transgenic plant according to the present invention is determined by any of various methods known in the art.

The impact of expression of proteins rich in tyrosine, lysine, serine, threonine or cysteine residues on lignin structure, chemical and morphological characteristics of the transgenic plants containing an expression cassette of the present invention is characterized by techniques such as histological staining, TEM, and confocal laser scanning microscopy, for instance to evaluate lignin distribution in the plant tissues. For example, nuclear magnetic resonance (NMR) and dynamic mechanical analyses are used to analyze lignin, wood tissue and/or other plant materials. Solid state NMR and solution NMR are used to investigate the structure and specific chemical environment of lignin nuclei, and the interaction of lignin with proteins rich in tyrosine, lysine, serine, threonine or cysteine residues. Dynamic mechanical analysis is used to probe changes in the lignin glass transition, believed to shift to a higher temperature due to the imparted cross linking.

Methods of Producing Fermentable Sugar from Transgenic Plants

A method of producing fermentable sugar from a lignocellulosic plant according to embodiments of the present invention includes providing a transgenic plant transformed with an expression cassette encoding a protein rich in tyrosine, lysine, serine, threonine or cysteine residues; and degrading lignocellulosic material of the plant.

In particular embodiments of the present invention, methods of producing fermentable sugar include removal or reduction of lignin in lignocellulosic material by contacting a transgenic plant according to the present invention or a part thereof with a peptidolytic agent. A peptidolytic agent is a substance having peptide bond cleaving activity. A protease enzyme is an example of a peptidolytic agent.

In particular embodiments of the present invention, methods of producing fermentable sugars from a transgenic lignocellulosic plant include contacting lignocellulosic material of the transgenic plant with one or more protease enzymes. Any enzymatic protease which degrades a protein in the lignocellulosic material can be used. Non-limiting examples of protease enzymes that can be used include proteinase K, papain, trypsin, chymotrypsin, pepsin, streptokinase or any plant, animal, fungal or bacterial protease. Proteases can be obtained commercially, chemically synthesized or isolated from an organism that expresses a protease. Conditions suitable for activity of a protease enzyme depend on the particular enzyme used and such conditions are well-known readily discernable by one of skill in the art.

Chemical methods are optionally used to hydrolyze peptide bonds in the lignocellulosic material of a transgenic plant and thereby reduce or remove lignin. For example, acid treatment of the lignocellulosic material of a transgenic plant can be used to degrade proteins and reduce or remove lignin. Acid peptidolytic agents include, but are not limited to, formic acid, acetic acid, trifluoroacetic acid, hydrochloric acid and sulfuric acid.

In particular embodiments of the present invention, methods of producing fermentable sugar include cleaving carbohydrates of lignocellulosic material by contacting a transgenic plant according to the present invention or a part thereof with a cellulolytic agent. A cellulolytic enzyme is an example of a cellulolytic agent.

Thus, embodiments of the present invention include contacting the lignocellulosic material with one or more cellulolytic enzymes under conditions suitable for activity of a cellulolytic enzyme. The cellulolytic enzyme can be any enzyme which hydrolyzes cellulose to release fermentable sugars such as glucose, mannose, xylose, galactose and arabinose. Cellulolytic enzymes include, but are not limited to, cellulases, hemicellulases, endoglucanases, cellulobiohydrolases, beta-glucosidases, esterases, laccases and peroxidases. Combinations of cellulolytic enzymes can be used to degrade lignocellulosic material. Cellulolytic enzymes can be obtained commercially, chemically synthesized or isolated from an organism that expresses a cellulolytic enzyme according to methods well-known in the art, for instance as described in U.S. Pat. No. 7,354,743. Conditions suitable for activity of a cellulolytic enzyme depend on the particular enzyme used and such conditions are well-known and readily discernable by one of skill in the art.

Fermentable sugars released from lignocellulosic material of transgenic plants of the present invention can be used to produce ethanol or other products including glycerol, other alcohols exemplified by methanol, sorbitol, xylitol and butanol. Ethanol and/or other products can be produced by fermentation of the fermentable sugars by suitable microorganisms, such as yeast, bacteria and fungi, using methods well-known in the art. Ethanol production is achieved, for example, by saccharification to release the fermentable sugars followed by fermentation or by simultaneous saccharification and fermentation.

Embodiments of inventive compositions and methods are illustrated in the following examples. These examples are provided for illustrative purposes and are not considered limitations on the scope of inventive compositions and methods.

EXAMPLES

Example 1

Expression Cassette

Figure 2:
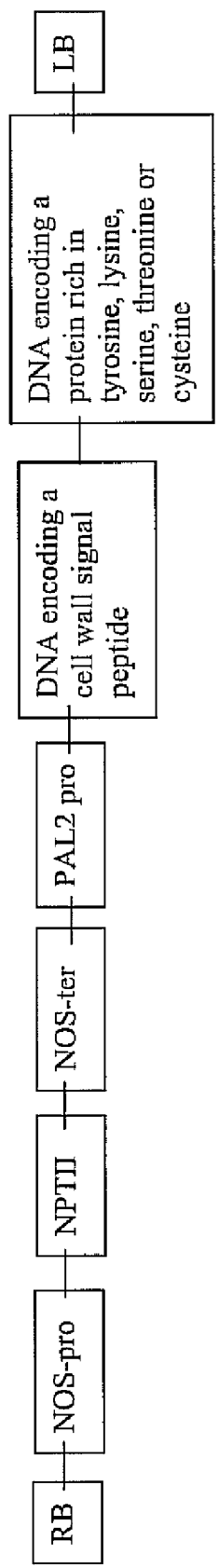
FIG. 2 is a schematic representation of an exemplary expression cassette of the present invention encoding a protein rich in tyrosine, lysine, serine, threonine or cysteine residues.

An exemplary expression cassette is shown schematically in FIG. 2.

A nucleic acid sequence encoding a protein rich in protein rich in tyrosine, lysine, serine, threonine or cysteine residues is fused to a leader sequence encoding a signal peptide to direct secretion into the cell wall and driven by a promoter to facilitate transgene expression in lignifying tissues. In this example, the promoter is the hybrid poplar, (*P. trichocarpa*× *P. deltoids*), PAL2. A particular example is the Pt4CL1P promoter and others described in Li, L. et al., Proc. Natl. Acad. Sci. USA, 100:4939-4944, 2003.

Also included in the illustrated cassette is a selection marker, a gene encoding antibiotic resistance for selection of transformed cells, such as the neomycin phosphotransferase II (NPTII) gene for kanamycin resistance. The NPTII gene is driven by a nopaline synthase (nos) promoter. Further included and shown in FIG. 2 is transferred DNA (T-DNA) right border (RB) and left border (LB). Further included in the illustrated cassette is a nopaline synthase gene terminator (nos-ter). Particular cassettes include the DNA sequence SEQ ID No. 2, 4, 6 or 8, a variant thereof or a fragment thereof, encoding a protein rich in protein rich in tyrosine, lysine, serine, threonine or cysteine residues.

Example 2

Vector Construction

An expression cassette as shown in FIG. 2 is constructed including the cDNA sequence SEQ D NO. 2. The expression cassette is cloned into binary vector pBI101 (Clontech, CA), replacing the β-Glucuronidase (GUS) gene. SEQ ID No. 2 encodes a tyrosine-rich hydroxyproline-rich glycoprotein gene from *Petroselinum crispum* (parsley), described in P. Kawalleck, et al., Two Pathogen-Responsive Genes in Parsley Encode a Tyrosine-Rich Hydroxyproline-Rich Glycoprotein (hrgp) and an Anionic Peroxidase, Mol. Gen. Genet. 1995, 247, 444-452, a protein in which 12% of total amino acid residues are tyrosine. The transgene includes a leader sequence derived from a lodgepole pine xylem β-glucosidase cDNA which is described in D. P. Dhannawardhana, et al., cDNA Cloning and Heterologous Expression of Coniferin β-Glucosidase, Plant Mol. Biol. 1999, 40, 365-372, which has been shown to direct secretion into the cell wall, see A. L. Samuels, et al., Cellular Machinery of Wood Production: Differentiation of Secondary Xylem in *Pinus contorta* var. *latifolia*, Planta, 2002, 216, 72-82. A poplar phenylalanine ammonia-lyase gene (PAL2) promoter, described in M. Gray-Mitsumune, et al., Plant Mol. Biol. 1999, 39, 657-669, is also included in the expression cassette as shown schematically in FIG. 2, to facilitate transgene expression in lignifying tissues. The resulting vector is further referred to herein as pPAL: TYR.

Example 3

Transgenic Lines

A total of 24 hybrid poplar "Ogy" transgenic lines are regenerated in this example. Using leaves and petioles as explants, hybrid poplar clone OGY are transformed with the pPAL:TYR construct by an *Agrobacterium*-mediated method. Briefly described, leaf explants (approximately 5 mm×5 mm) and petioles cut from young "Ogy" leaves are pre-cultured in initiation medium containing Murashige and Skoog salts base (4.3 g/l Murashige & Skoog salt mixture (Murashige and Skoog, 1962), 0.109 g/l 1000× Nitsch & Nitsch vitamin mixture (Nitsch and Nitsch, 1969), 10 mM $CaCl_2$, 30 g/l sucrose, 10 mg/l thiamine HCl, 100 mg/l myo-inositol) with 1.0 μM α-naphthaleneacetic acid (NAA), 1.75 μM 6-benzylamino-purine (BAP), pH 5.7 for 48 h in the dark. Leaf explants are then co-cultured for 2 d with $10^9$ cells/ml of *A. tumefaciens* which is suspended in initiation medium (pH 5.4) with 0.1 mM acetosyringone. After co-cultivation, the explants are transferred into the initiation medium (pH 5.7) containing 100 μg/ml kanamycin, 200 μg/ml carbenicillin and 100 µg/ml cefotaxime for selection and shoot induction. After 4-5 weeks, 0.5-1.0 cm-long adventitious shoots, regenerated from leaf explants in the initiation medium are excised and transferred directly to the rooting medium (2.3 g/l McCown's woody plant basal mixture (Lloyd and McCown, 1981), 0.109 µl 1000× Nitsch & Nitsch vitamin power, 10 mM $CaCl_2$, 30 g/l sucrose, 10 mg/l thiamine-HCl, 100 mg/l myo-inositol, 2.0 µM NAA, 7.5 g/l agar, pH 5.7) containing 35 µg/ml kanamycin, 200 µg/ml carbenicillin and 100 µg/ml cefotaxime for root induction. Only shoots that rooted in the rooting medium are transferred into the shooting medium (MS base with 1.0 µM NAA, 0.5 µM BAP, 7.5 µl agar, pH 5.7) with 50 µg/ml kanamycin, 200 µg/ml carbenicillin and 100 µg/ml cefotaxime for shoot elongation. Plants are then regenerated from the leaves of the putative transformants using the initiation, rooting, and shooting media method as described above except that no carbenicillin and cefotaxime are included in the media. The cultures are then monitored for any *Agrobacterium* growth during regeneration. The resulting plantlets are potted in artificial potting mix containing equal volumes of perlite, peat moss, and vermiculite and then acclimatized in a growth chamber by gradually opening the ventilation ports on the top. Routine in vivo rooting, propagation, and regeneration of transformed and control plants are carried out in a growth chamber at 22±2° C. under a 16-h photoperiod of cool-white fluorescent light (photon flux of 35 µmol $m^{-2}$ $s^{-1}$). No obvious abnormal morphology is observed in any of the transgenic plants grown under greenhouse conditions when compared to untransformed controls.

Example 4

Stable Transformation Events are Confirmed by Southern Hybridization

For Southern hybridization analysis, genomic DNA is extracted from young leaves of transgenic and wildtype plants. Approx. 10 µg of genomic DNA is digested with XbaI, and then size fractionated via electrophoresis in a 1% agarose gel and transferred to Hybond N membrane (Amersham, N.J.). The membrane is hybridized with a digoxigenin-dUPT labeled DNA probe corresponding to the transgene. DNA Ladder I shown is obtained from GeneChoice, Inc, MD. Filter hybridization, using the DIG high Prime DNA Labeling and Detection Starter Kit I, is conducted according to the standard instructions of the manufacturer (Roche Diagnostics, IN).

Example 5

Expression of the Transgene

Figure 3:
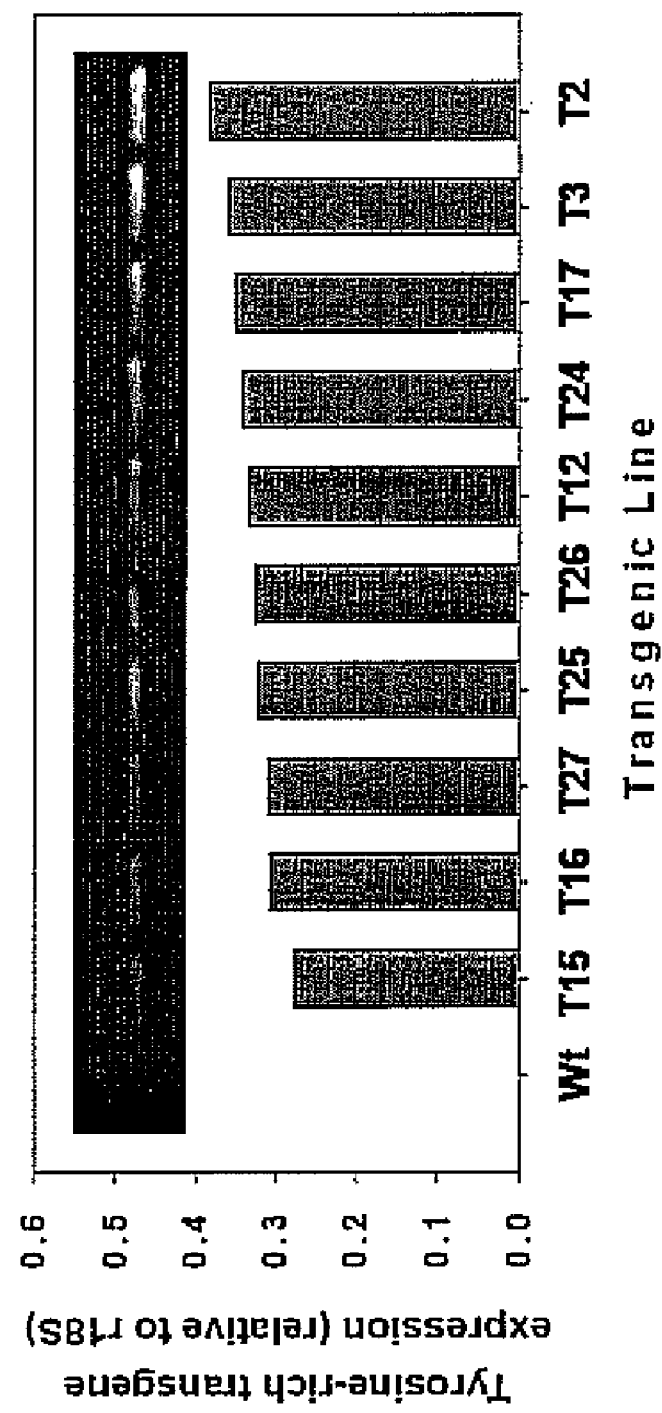
FIG. 3 is a graph showing expression of a tyrosine-rich transgene in transgenic plants of the present invention quantified from real-time RT-PCR results, shown in the inset, performed on material derived from the transgenic plants.

Total RNA is extracted from stem tissues of various transgenic lines and wildtype plants to confirm transgene expression. Entire stem tissue is harvested directly into liquid $N_2$ and ground to a powder in a mortar and pestle. Total RNA is extracted using a modified CTAB method, treated with DNAse (turbo DNAse, Ambion, Tex.) to remove any residual DNA contamination, and then reverse transcribed to single strand cDNA following manufacturer's instructions (SuperScript™ III Reverse Transcriptase, Invitrogen, CA). Real-time quantitative RT-PCR is conducted using SYBR Green-based detection with transgene-specific primers Forward: 5'AAATTTGCATTGGGGCATTA3' SEQ ID No. 9; Reverse: 5'AGACTTGGAAGGTGGTGGTG3' SEQ ID No. 10. Ribosomal 18S specific PCR primers, Forward: 5'AAACGGCTACCACATCCAAG3' SEQ ID No. 11; Reverse: 5'CCCAACCCAAAGTCCAACTA3' SEQ ID No. 12, are used to amplify ribosomal 18S RNA and transgene expression is normalized to 18S RNA. For each primer pair, melting curves confirmed that single amplicons are amplified during experimental runs and allowed setting of gene-specific read temperatures to ensure specificity of fluorescence readings. FIG. 3 shows PCR results and a graph indicating levels of expressed transcripts normalized to ribosomal 18S. Bars represent individual samples from each transgenic line.

Example 6

Lignin Content and Morphology of Transgenic Plants

No significant changes are observed in transgenic stem tissues in terms of lignin content and micron-scale morphology. Transverse stem sections from internodes between leaf plastochron index 8 & 9 (growth stages) are stained with potassium permanganate or phloroglucinol-HCL as described in D. Guo, et al., Plant Cell 2001, 13, 73-78. Since the intensity of phloroglucinol staining is associated with lignin content [N. G. Lewis, E. Yamamoto, Lignin: Occurrence, Biogenesis and Biodegradation. Ann. Rev. Plant Physiol. 1900, 41, 455-496.] and potassium permanganate staining is specific to syringyl moieties [G. Meshitsuka, J. Nakano, Studies on the Mechanism of Lignin Color Reaction. Mäule Color Reaction, Mokuzai Gakkaishi, 1978, 25, 588-594.], these results indicate that there are no changes in overall lignin content or in S lignin content in the transgenic lines compared to wild-type.

Figure 4:
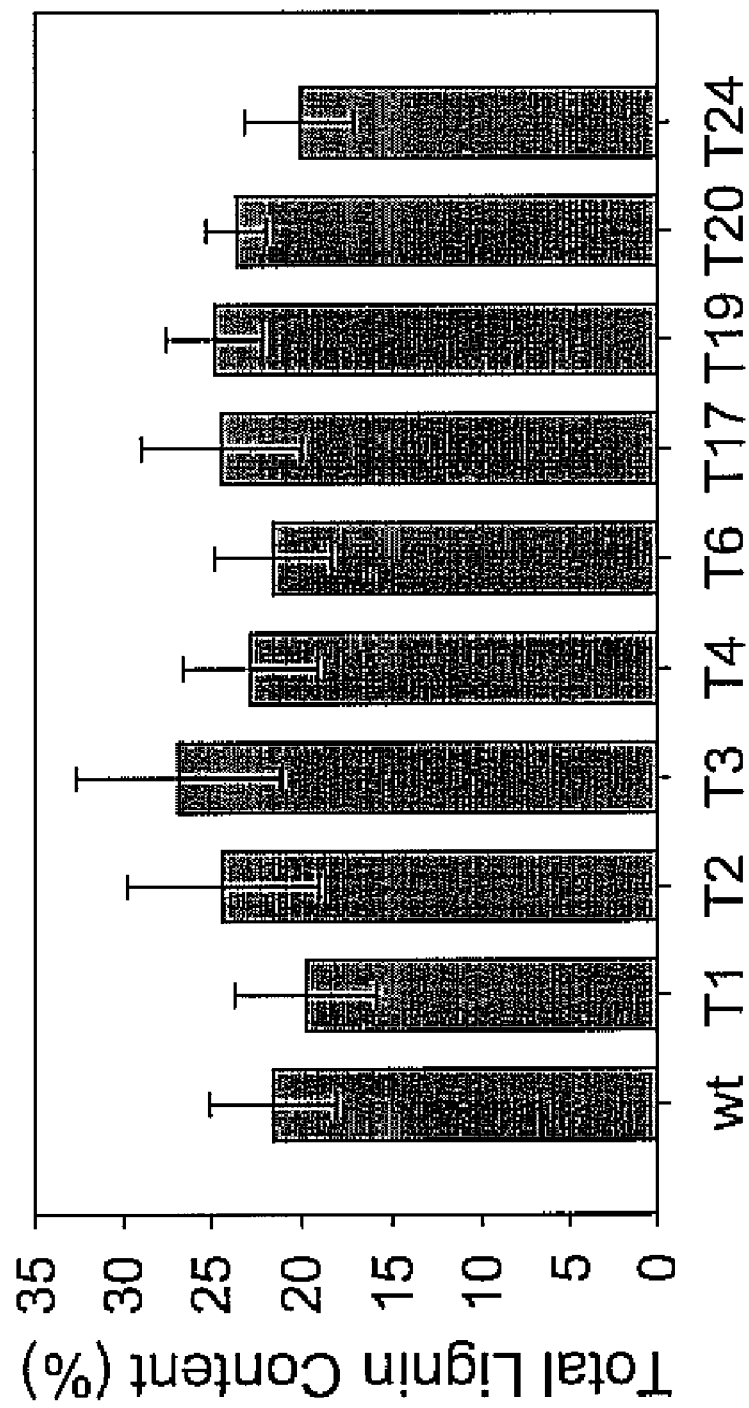
FIG. 4 is a graph showing results of an assay for lignin content in transgenic plants of the present invention compared to wild-type plants.

This finding is further confirmed by lignin content assay using the Klason method. Stems are collected from 4 plants for wildtype "Ogy" and at least 3 for each transgenic line. Lignin content in stems from internodes between leaf plastochron index 3-19 is analyzed by Klason method ($H_2SO_4$ extraction), described in detail in O. Theander, E. Westerlund, J. Agric. Food Chem. 1986, 34, 330-336. The assay is run with 3 replicates for each sample. Stems are ground by Wiley Mill and subjected to 101° C. overnight drying before weighing. FIG. 4 shows the results indicating lignin content represented as percentage of stem dry weight. Bars are means±standard deviation (SD) of three biological replicates. ANOVA analysis indicates that there are no significant differences in lignin content among wildtype "Ogy" and transgenic lines. In addition, no significant differences are observed in lignin content among the trees within the same genotype.

Example 7

Digestibility Assays in Transgenic Plants

Figure 5:
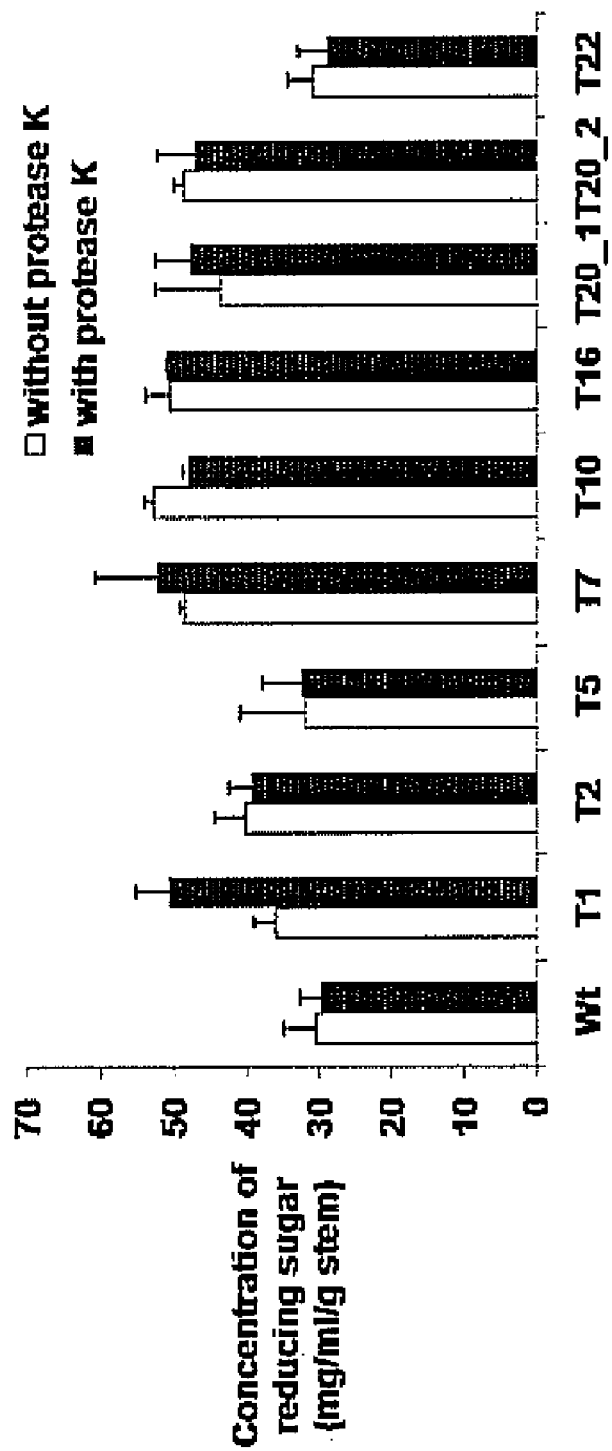
FIG. 5 is a graph showing results of an assay for release of fermentable sugars from transgenic plants of the present invention compared to wild type plants, where the transgenic and wild-type plants are treated with cellulolytic enzymes cellulase and hemicellulase, white bars, or treated with a protease, and treated with cellulase, and hemicellulase, dark bars.

The digestibility of the stem tissue is assayed using protease K and/or cellulase/hemicellulase. Stem tissue is collected, dried at room temperature for at least 1 week, and then ground into small particles with a Wiley Mill fitted with a 1 mm screen. Approximately 0.1 g ground tissues are rehydrated with 1.5 ml Tris buffer (50 mM Tris-HCL, 1 mM $CaCl_2$, pH 8.0) at 37° C. for 5 hours, then 15 microliters of proteinase K (100 mg/mL) or Tris buffer are added to the samples. After an overnight incubation at 37° C. with shaking, 180 microliters of the supernatant from each sample are subjected to hydrolytic digestion with cellulase and hemicellulase overnight at 45° C. with shaking. Hydrolytic digests are conducted in 800 microliters of 5 mM citrate buffer (pH 4.5) with 10 microliters each of cellulase and hemicellulase (100 mg/mL). The concentration of reducing sugar in each sample is then detected by tetrazolium blue method as described in R. Mullings, I. H. Parish, Enzyme Microb. Technol. 1984, 6, 491-496, and represented as milligrams of reducing sugar per milliliter per gram of stem tissue. There are at least two experimental repeats for each sampling plant. Two biological replicates (two plants) are included for transgenic line T20. Data are analyzed by ANOVA with statistical significance evaluated at $\alpha$=0.05. FIG. 5 shows a bar graph illustrating the release of sugars from wild-type and pPAL:TYR transgenic plant material with and without protease K treatment. For each transgenic line, a portion of ground tissue is incubated with sequential incubations of protease K followed by cellulase and hemicellulase (shaded bars), while another portion of tissue is incubated only with cellulase and hemicellulase (open bars). Bars are means±SD of 2-3 replicates of individual saplings.

Of the lines surveyed, two lines, T1 and T7, show significant differences in the amount of sugar released from stem digestions pre-treated with protease K, relative to those without protease treatment as shown in FIG. 5, p=0.0017, 0.0380, respectively for T1 and T7. For line T1, the digestibility of the non-protease treated stem tissue is similar to the wild-type. In most of the transgenic lines, significantly more polysaccharides are released than from wild-type, independent of protease K treatment.

Thus, expression of proteins rich in protein rich in tyrosine, lysine, serine, threonine or cysteine residues in transgenic plants produces no noticeable pleiotropic effects on plant morphology or growth rates. In addition, provided modified plant tissues according to methods of the present invention exhibit enhanced digestibility after enzyme and/or protease treatment.

Example 8

Fitness of Transgenic Plants

Transformants are analyzed for stability of inserts, for lignin content and for the presence and the localization of the TYR-rich peptides. Transformed "Ogy" is compared to wild type in terms of growth rate, form, disease resistance, wood production, and basic wood physical properties, such as specific gravity and/or tensile strength. No significant morphological or growth differences are noted.

To assess the structural rigidity of the stem tissues, dynamic mechanical analysis (DMA) is conducted using a TA Instruments DMA Q800 fitted with a single cantilever clamp. Rectangular samples measuring 25 mm×10 mm×2 mm are cut from poplar stems. The long axis of the sample is parallel to the grain. Samples are equilibrated for approximately 1 week at 35° C. prior to analysis. Clamps are tightened to 6 psi of torque to ensure uniform clamping pressure. An analysis of the linear viscoelastic region (LVR) determines that an amplitude of 18 µm is suitable for the test protocol.

Figure 6:
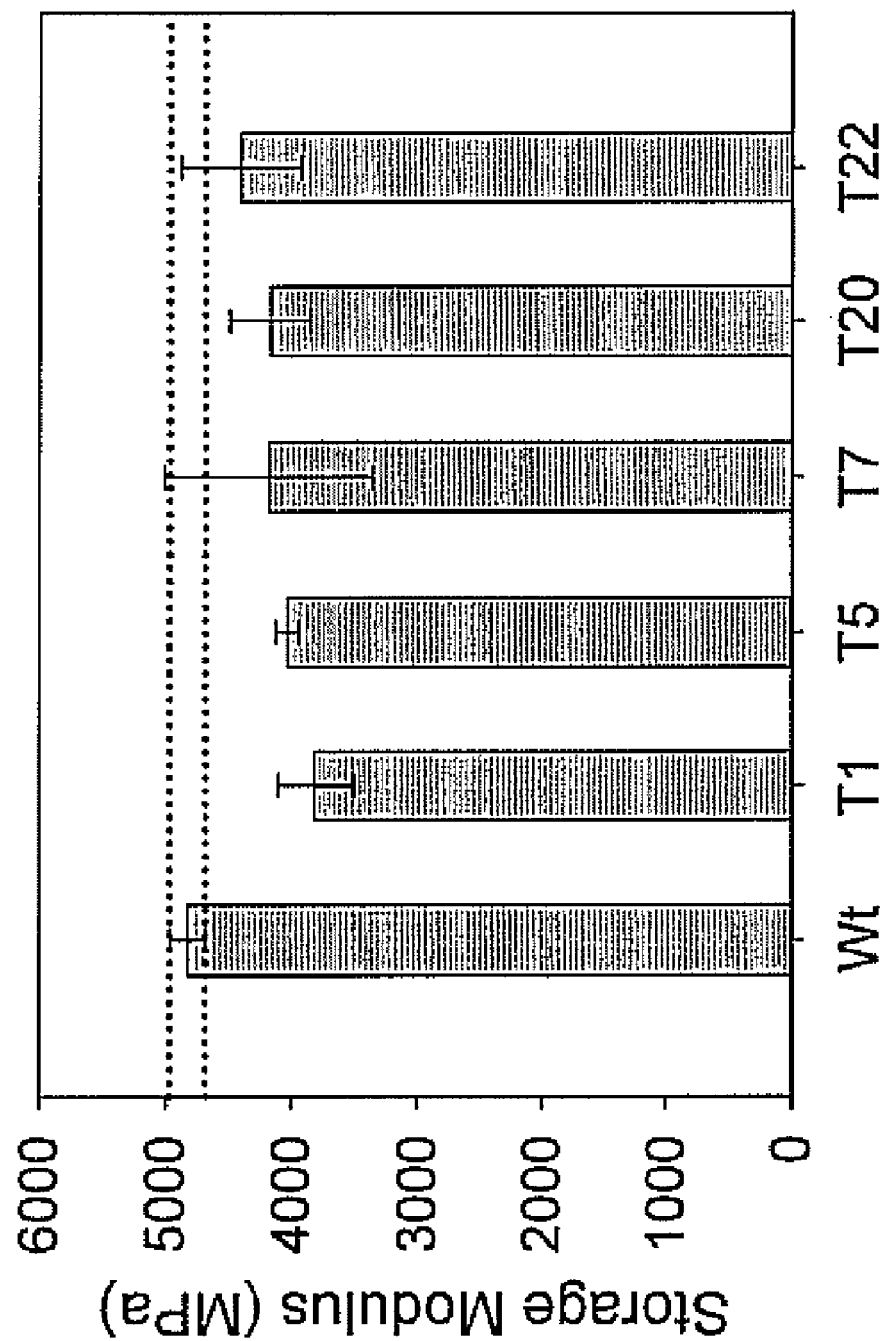
FIG. 6 is a graph showing results of an assay of tensile strength performed on transgenic plants of the present invention and wild-type plants.

For DMA analysis, each sample is removed from the oven, clamped in the DMA Q800, equilibrated at 35° C., and analyzed at 1 Hz. Five replicate measurements are made on each sample. Two different samples are analyzed for each transgenic line, each from the same sapling unless otherwise noted. Results are shown in FIG. 6.

Example 9

An expression vector including an expression cassette is constructed including the cDNA sequence SEQ ID NO. 4 operably linked to a promoter. The expression cassette is cloned into binary vector pBI101 (Clontech, CA), replacing the β-Glucuronidase (GUS) gene. The transgene encodes a signal peptide operably linked to glycine-rich cell wall structural protein 1.8 precursor (GRP 1.8).

Example 10

An expression vector including an expression cassette is constructed including the cDNA sequence SEQ ID NO. 6 operably linked to a promoter. The expression cassette is cloned into binary vector pBI101 (Clontech, CA), replacing the β-Glucuronidase (GUS) gene. The transgene encodes a signal peptide linked to glycine-rich cell wall structural protein 1.0 precursor (GRP 1.0).

Example 11

An expression vector including an expression cassette is constructed including the cDNA sequence SEQ ID NO. 8 linked to signal peptide encoding SEQ ID No. 16, both of which are operably linked to a promoter. The expression cassette is cloned into binary vector pBI101 (Clontech, CA), replacing the β-Glucuronidase (GUS) gene. The transgene encodes an artificial protein operably linked to the signal peptide derived from a lodgepole pine xylem β-glucosidase cDNA (SEQ ID No. 13).

Example 12

Eucalyptus transformation with an expression is accomplished by co-cultivation of leaf explants harvested from in vitro shoot cultures. Typical disarmed *Agrobacterium tumefaciens* strains such as LBA4404 containing a standard binary vector are used. Stably transformed callus is obtained by selection for kanamycin resistance and visual reporter genes such as gus. Transgenic shoots are regenerated efficiently from the callus within 3 months. Transgenic shoots are maintained indefinitely in culture or rooted, in the absence of hormones, and transferred to the greenhouse.

Example 13

Pines are stably transformed by cocultivation of either dry embryos from seeds (e.g., Tang, et al. (2007) Journal of Experimental Botany 58(3); 545-554) or of embryogenic tissue cultures (e.g. Cerda et al. (2002) Plant Cell, Tissue and Organ Culture 70 251-257) using *Agrobacterium tumfaciens* strains such as EHA101 containing standard binary vectors carrying genes for selectable markers such as GFP and antibiotic resistance. With seed embryos, kanamycin-resistant calli are produced from which transgenic shoots are regenerated followed by rooting of individual shoots. With embryogenic tissue cultures, secondary embryogenesis is induced concurrently with selection for antibiotic resistance and then transgenic plants are obtained through maturation and germination of the somatic embryos.

Example 14

Several spruce species, including *Picea glauca, P. mariana* and *P. abies* are transformed by *Agrobacterium tumefaciens*. (e.g. Klimaszewska et al. (2001) *In Vitro Cellular and Developmental Biology Plant* 37 748-755) by cocultivation of somatic embryogenic tissue cultures with typical *Agrobacterium tumefaciens* strains such as EHA101 containing standard binary vectors carrying genes for selectable markers such as GFP and antibiotic resistance. Transgenic plants are obtained efficiently after maturation and germination of the somatic embryos from antibiotic-resistant embryogenic tissue cultures following secondary embryogenesis. The transgenic embryogenic tissue cultures can be maintained indefinitely under selection. Plants obtained via somatic embryogenesis are as vigorous as normal seedlings and perform well when transferred into the greenhouse and then into field plantations.

Example 15

A simple protocol for transformation and regeneration of alfalfa (e.g. Shao et al (2000) Plant Growth Regulation 31:155-166) includes cocultivation of leaf explants with standard disarmed *Agrobacterium tumefaciens* strains such as EHA101 and LBA 4404 carrying typical binary vectors, followed by selection of antibiotic resistant calli from which somatic embryos are induced, matured and germinated. This protocol is efficient and quick, providing transgenic plants within 10 to 14 weeks.

Example 16

Maize is transformed reliably via *Agrobacterium* with essentially the same methods as for transformation of poplar (e.g. Frame, B. R., McMurray, J. M., Fonger, T. M., Main, M. L., Taylor, K. W., Torney, F. J., Paz, M. M., Wang, K. (2006) Improved *Agrobacterium*-mediated transformation of three maize inbred lines using MS salts. Plant Cell Rep 25: 1024-1034). Maize (*Zea mays*) transformation is accomplished through cocultivation of immature zygotic embryos, that have been aseptically dissected from ears of greenhouse-grown plants 10 to 13 days post pollination, for 10 to 13 days with a broad host range *Agrobacterium tumefaciens* such as strain EHA101 containing a standard binary vector carrying the gene(s) of interest. The bar marker gene and the gus reporter gene work best for selection of stably transformed embryos, from which embryogenic callus develops. After 3 to 4 weeks transgenic plants are regenerated via maturation and germination of bialaphos-resistant somatic embryos.

Example 17

Analysis of Lignin in Transformed Plants

Lignin Histological Staining.
Stems of transgenic poplar are hand-sectioned and fixed. Fixed tissue sections will be stained for lignin using phloroglucinol/HCl (5% in n ethanol/HCl mix 9:1) and potassium permanganate.

Lignin Content and Composition.
Traditional lignin analyses are conducted on dry, stem tissues from both transgenic plants and control plants. Total lignin content is determined following the standard Klason method, as detailed in Dence, C., Lignin determination, in Methods in Lignin Chemistry, S. Lin, Editor. 1992, Springer-Verlag: Berlin. p. 33-61. Thioacidolysis will be completed as described by Lapierre, C. et al., 1999, Plant Physiol. 119, 153-163, in order to determine syringyl to guiacyl ratios.

Localization of Expressed Tyrosine- and/or Cysteine-Rich Proteins in Transgenic Plants
Proteins can be expressed heterologously in *E. coli* using the pET21 vector, and incorporating a His tag for ease in purification and also for use of anti-his tag antibodies for localization. Antibodies are used to visualize the peptides in the cell walls of modified plants by immunolocalization. Immunolocalizations are carried out on stem sections bound to Vectabond coated slides, for example, as per the protocol of Amarasinghe, V. et al., 1994, Can. J. Bot.-Rev. Can. Bot. 72, 788-793. Poplar stem sections will be prepared as per Gray-Mitsumune, M., et al., 1999, Plant Mol. Biol. 39, 657-669. Sections are blocked with 10% goat serum. Peptide antisera are used at a 1:100 dilution at 37° C. for 3 hrs followed by 1:160 dilution of anti-rabbit IgG-FITC conjugate (Sigma) for 2 hrs at 37° C. Imaging is conducted by confocal laser scanning microscopy. Controls are performed by omitting the primary antibody, and by co-localization with antibodies to known lignin pathway extracellular proteins (laccase or peroxidase). High resolution definition of the subcellular location of the transgenic peptides is determined by TEM on cryosections and immunogold labeling.

Evaluating Lignin Cross Linking and Lignin-Tyrosine and/or Lignin-Cysteine Interactions
NMR spectroscopy and Dynamic Mechanical Analyses (DMA) are used to probe the effects of tyrosine and/or cysteine-rich proteins on lignin structure and morphology in transgenic plants of the present invention. Liquid state NMR, such as described in Hu, W. J. et al., 1999, Nat. Biotechnol. 17, 808-812., is used to investigate the lignin structure by isolating milled wood lignin from modified stem tissues and performing proton-detected HSQC (heteronuclear single-quantum coherence) and total correlation spectroscopy (TOCSY).

Solid-state (cross polarization/magic angle spinning, CP/MAS) NMR experiments may be conducted on the modified stem tissues. The tyrosine and/or cysteine-rich proteins produced with a $^{15}N$ label by supplying the plants with $K^{15}NO_3$, as described in Engelsberger, W. R. et al., 2006, Plant Methods. 4, 1-11. In order for cross-polarization to succeed, hydrogen atoms in the lignin must be within a given molecular proximity of the $^{15}N$ protein (typically less than 10 angstroms) and have sufficient rigidity for cross-polarization to occur. Different $^{15}N$ chemical shifts should be detected for the various amino acids constituting the proteins, allowing the angstrom scale miscibility of tyrosine and/or cysteine; and lignin, as well as tyrosine and/or cysteine; and cellulose, to be probed.

In addition, the proton spin-lattice relaxation time in the rotating frame ($^{H}T_{1p}$) for the nuclei in the protein and the lignin are quantified. A common $^{H}T_{1p}$ (regardless of the carbon or nitrogen resonance being monitored) indicates nanoscale homogeneity, while different $^{H}T_{1p}$s indicate nanoscale phase separation. This data is collected via variable contact time cross polarization experiments. It is appreciated that nuclear relaxation times are in themselves an indication of chemical structure. A more highly networked lignin will have different characteristic nuclear relaxation times than the control lignin.

Dynamic mechanical analyses provide complementary information to NMR, investigating polymer relaxations on a broader scale. In this technique, tissue samples are fixed in clamps as small mechanical perturbations are applied, allowing frequency-dependent polymer segmental relaxations to be detected. The glass transition of lignin in wood is indicated by a characteristic damping peak via DMA, and the impact of the cross linking induced through the tyrosine-rich protein will be quantified through assessing the onset, breadth, and frequency-dependent nature of the glass transition.

Example 18

TMAH thermochemolysis analysis. Lignin structure can be analyzed by tetramethylammonium hydroxide (TMAH) thermochemolysis, depolymerizing lignin into its aromatic subunits by breaking β-O-4 linkages, and methylating all ring hydroxyls as described in T. R. Filley, in *Wood Deterioration and Preservation*. (2003), vol. 845, pp. 119-139. The resulting product is then analyzed by GC/MS to determine how the lignin structure has been chemically modified. In undegraded wood, the predominant products from TMAH thermochemolysis have been identified as described in T. R. Filley, in *Wood Deterioration and Preservation*. (2003), vol. 845, pp. 119-139 and this method can be used to identify lignin-tyrosine linkages. If the tyrosine crosslink occurs with a subunit that is also linked through β-O-4 linkages, then the structure shown in Scheme 3 (right) would be identified by GC/MS. TMAH thermochemolysis is performed with the modified method described in Frazier, S. W. et al. Characterization of organic matter from natural waters using tetramethylammonium hydroxide thermochemolysis GC-MS. Journal of Analytical and Applied Pyrolysis. 70, 99-128 (2003). Approximately 0.5 mg of each sample and 150 µL of TMAH (25 wt. % TMAH in methanol, Fisher Scientific) are placed in borosilicate glass tubes and mixed by vortexing for 30 s. The samples are dried under nitrogen and vacuum-sealed on a manifold prior to being baked at 250° C. for 30 min. The sealed tubes are allowed to cool before cutting the glass and adding an internal standard, linolenic acid methyl ester (Sigma Aldrich) at 54.2 ng/µL in ethyl acetate. Samples are extracted from tubes by washing the sides of the tubes with ethyl acetate (Fisher Scientific). All washings (approx. 1 mL per sample) are filtered through glass wool, combined, and concentrated to 200 µL under a stream of nitrogen. The samples are analyzed by capillary GC-MS on a Hewlett Packard 6890 series GC system connected to a Pegasus III time-of-flight mass spectrometer (LECO Corporation, MI). The column used for the GC separation is a 15 m×0.25 mm (i.d.) fused silica capillary column with a film thickness of 0.25 µm (5% phenylpolysiloxane—95% methylpolysiloxane, Restek Rtx-5). The samples (1 µL) are injected onto a split/splitless injector operating in splitless mode at a temperature of 280° C. The column, using helium as the carrier gas, is run with a constant flow (1.0 mL/min), and the oven temperature is held initially at 50° C. for 2 min, then ramped from 50 to 300° C. at 15° C./min, and then held at 300° C. for 6.33 min, giving a total run time of 25 min. The ionization mode on the mass spectrometer is electron ionization at 70 eV, and the ion source temperature is 200° C. while the transfer line temperature is 280° C.

Scheme 3 shows lignin linked to a tyrosine residue of a protein encoded by an expression cassette in a transgenic plant of the present invention through carbon-carbon bond of the aromatic rings. TMAH thermochemolysis results in formation of a tyrosine-lignin dimeric adduct which can be detected by GC/MS. Each R in Scheme 3 represents an amino acid residue of the protein bonded to lignin.

Scheme 3

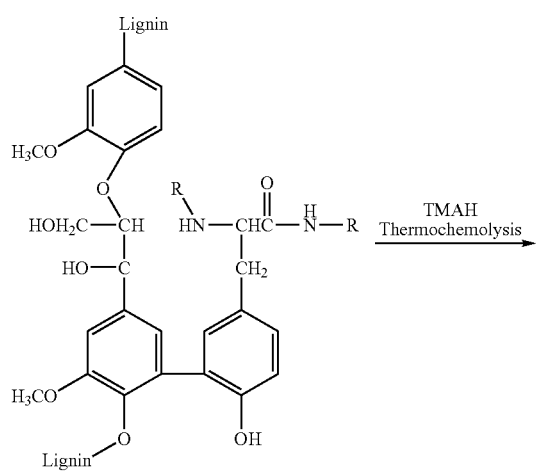

-continued

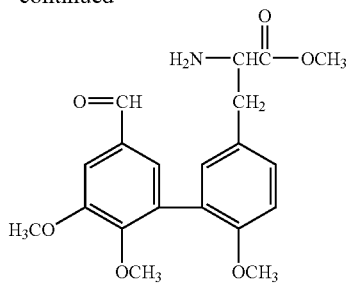

Example 19

Pulping and Ethanol Production Assessment

Modified tissues are evaluated to yield quantitative information regarding pulp yields and ethanol yields. The effect of the protease treatment on both pulping and ethanol production will be quantitatively investigated. In vitro digestibility of the wood after protease pretreatment is evaluated. Protease treatment may be performed as described above. In vitro digestibility is performed by measuring release of reducing sugars.

Pulp yield is determined as detailed by Stewart, J. J. et al., 2006, Holzforschung. 60, 111-122. NREL (National Renewable Energy Laboratory) analytical procedures regarding cellulose biomass processing are used, for example, as described in Sluiter, A., B. et al., Determination of Structural Carbohydrates and Lignin in Biomass, Laboratory Analytical Procedure, Technical Report NREL/TP-510-42618, Apr. 25, 2008; and Sluiter, A., B. et al., Determination of Sugars, Byproducts, and Degradation Products in Liquid Fraction Process Samples, Laboratory Analytical Procedure, Technical Report NREL/TP-510-42623, Issue Date Dec. 8, 2006.

The yield of ethanol produced from the transgenic plants according to the present invention can be measured using gas chromatography, for example as described in Templeton, D. W., "Determination of Ethanol Concentration in Biomass to Ethanol Fermentation Supernatants by Gas Chromatography" Templeton, D. W., 1994, National Renewable Energy Laboratory (NREL) Laboratory Analytical Procedure 011.

Example 20

Disease Resistance Tests

Disease susceptibility of transgenic plants according to the present invention to *Septoria musiva* is evaluated by an in vitro leaf disk assay as per protocol described in Liang, H. Y. et al., 2001, Plant Mol. Biol. 45, 619-629. *S. musiva* is one of the most damaging pathogens in poplars, causing leaf spots, early leaf drop and canker diseases. Briefly, *S. musiva* conidia, collected from V8 agar culture plates, are used to inoculate transformed and wild-type hybrid poplar "Ogy" leaf disks (15 mm in diameter). After two weeks of incubation at 22° C. under a 16 hr photoperiod of cool-light fluorescent light, percentage of necrotic area from transgenic and wild-type "Ogy" are scored by the NIH Image 1.61 program and compared.

Sequences Referred to Herein.

SEQ ID NO. 1 Tyrosine-rich hydroxyproline-rich glycoprotein from *Petroselinum crispum* (parsley). Amino acid sequence, including the translated leader sequence from beta-glucosidase from *Pinus contorta*.

```
Met E V S V L Met W V L L F Y S L L G F Q V T T A
R L D R N N F P S D F Met F G T A S S A Y Q Y E G
A V R E D G K G P Y H S P P P P V K S P P P P Y Y
Y S S P P P P V K S P P P P Y Y Y T S P P P P V K
S P P P P Y Y Y T S P P P P Met K S P P P P Y Y P
H P H P H P H S Y T V K V V G K V Y C Y R C Y D W
K Y P I K S H A K K H L K G A V V E V T C K A G D
K D V V T Y G K T K I N G K Y S I T V K G F E Y G
K Y G G A K A C K A K L H Met A P K D S K C N I P
T N L H W G I K G A K L K V K S K S K Y E V V L S
A K P F A Y A P K T P Y K K C Y K P V P T P A A P
L T P P Y Y Y Q S P P P P S K S P A P T P Y Y Y K
S P P P P T K S P A P T P Y Y Y K S P R Stop
```

SEQ ID No. 2 DNA sequence encoding Tyrosine-rich hydroxyproline-rich glycoprotein from *Petroselinum crispum* (parsley) and the leader sequence from beta-glucosidase from *Pinus contorta*.

```
ATGGAGGTGTCTGTGTTGATGTGGGTACTGCTCTTCTATTCCTTATTAGG
TTTTCAAGTGACGACAGCTAGGCTGGACAGGAACAAcTTCCCCTCAGATT
tCaTGTTCGGCACAGCCTCTTCAGCGTATCAGTATGAAGGAGCAGTCCGA
GAAGATGGCAAGGGTCCTTATCACTCTCCACCACCACCCGTAAAATCCCC
ACCACCACCTTACTACTACTCATCACCACCACCACCCGTAAAATCCCCAC
CACCTCCATACTACTACACTTCACCACCACCACCAGTAAAATCCCCACCA
CCACCTTACTACTACACCTCTCCACCACCACCAATGAAATCCCCACCTCC
TCCTTACTACCCTCACCCTCACCCTCACCCTCATTCATACACAGTGAAAG
TTGTGGGAAAGGTCTACTGTTACAGATGCTATGACTGGAAGTACCCAATC
AAGTCCCATGCAAAGAAACACCTCAAAGGTGCGGTTGTTGAGGTGACATG
CAAGGCAGGAGACAAAGATGTAGTGACATATGGTAAAACAAAGATCAATG
GTAAATATAGCATCACAGTTAAAGGATTTGAGTATGGAAAATATGGTGGA
GCTAAGGCATGCAAAGCTAAGCTTCATATGGCACCAAAGGATTCTAAATG
TAACATACCAACAAATTTGCATTGGGGCATTAAGGGTGCAAAACTAAAAG
TGAAATCAAAGAGCAAATATGAAGTTGTTTTGTCTGCCAAACCTTTTGCT
TATGCTCCCAAAACTCCTTACAAGAAGTGTTATAAGCCTGTGCCAACACC
AGCAGCTCCTTTGACACCACCTTACTATTATCAGTCTCCACCACCACCTT
CCAAGTCTCCGGCACCAACTCCTTACTACTATAAGTCTCCTCCACCGCCT
ACGAAATCTCCGGCGCCGACTCCTTATTACTATAAGTCCCCACGATGA
```

SEQ ID No. 3 Amino acid sequence of Glycine-rich cell wall structural protein 1.8 precursor (GRP 1.8).

```
  1 MATIHRLPSL VFLVLLALGV CSARRALLTL DAGYGLGHGT GGGYGGAAGS YGGGGGGSG
 61 GGGGYAGEHG VVGYGGGSGG GQGGGVGYGG DQGAGYGGGG GSGGGGVAY GGGGERGGYG
121 GGQGGGAGGG YGAGGEHGIG YGGGGGSGAG GGGGYNAGGA QGGGYGTGGG AGGGGGGGGD
181 HGGGYGGGQG AGGGAGGGYG GGGEHGGGGG GGQGGGAGGG YGAGGEHGGG AGGGQGGGAG
241 GGYGAGGEHG GGAGGGQGGG AGGGYGAGGE HGGGAGGGQG GGAGGGYGAG GEHGGGAGGG
301 QGGGAGGGYG AGGEHGGGGG GGQGGGAGGG YAAVGEHGGG YGGGQGGGDG GGYGTGGEHG
361 GGYGGGQGGG AGGGYGTGGE HGGGYGGGQG GGGGYGAGGD HGAAGYGGGE GGGGGSGGGY
421 GDGGAHGGGY GGGAGGGGGY GAGGAHGGGY GGGGGIGGGH GGNVP
```

SEQ ID No. 4 DNA sequence encoding Glycine-rich cell wall structural protein 1.8 precursor (GRP 1.8).

```
  1 ttaacaaatt tataaaaaag aggtatgttt gcagttgcac ccgatgatag tggtggcaat
 61 aagaaaaaaa agggaagaca gaaggaagaa gaagattgag aaagtaaaat gcagtgcaaa
121 atggtggtga gtgggaggta gaaaagaggg ataggtaggt atgaaaaaga aagaaaaaa
181 gcgtaggttt gttggagtag ctagtgtatt tgtatgggta ctgcatgctc cgttggatgt
241 ggaagacagc agaagcacac aatgaagrtc cagtatgagt ggtttcagtg tatctttgta
301 tgttaacata atgggccaca ctgtggggca tccaactttc atatccatga gcttcaacca
361 ctctttgctc tcaacgagcc ttcccaatcc ctataaatac ccttcaagtc tcctcacttc
421 aaaaccaacc tatttcagct tcacttcact ctcatggcta ctattcacag gcttcccagt
481 ctagttttct tagtactatt ggctctaggt gtatgttctg ctagaagggc ccttctcacc
541 cttgatgctg gatatggttt aggtcatggc actggtggtg gttatggtgg tgctgctgga
```

-continued

```
 601 agttatggag gtggtggagg tggcggctcg ggtggtggcg gtggatatgc tggggagcat
 661 ggagttgttg ggtatggagg tggtagtggc ggaggtcaag gtgggggagt aggatatggt
 721 ggtgatcaag gagctggata tggtggtggt ggtggaagtg gtggtggtgg tggtgtggct
 781 tacggtggtg ggggagagcg tggtggttat ggtggaggtc aaggaggtgg agctggaggg
 841 ggatatggag ctggtggaga acatggcatt gggtatggag gaggtggcgg aagtggtgct
 901 ggtggtggag gtgggtataa tgctggagga gcacagggtg gtggatatgg tactggtgga
 961 ggagctggtg gcggtggtgg tggaggagga gatcacggtg gtggttacgg gggtggtcaa
1021 ggagctggag gtggagcagg tggagggtat ggtggtggtg gagagcatgg aggtggaggt
1081 ggtggtggtc aaggaggtgg agctggtgga ggatatggtg caggtggaga gcatggaggt
1141 ggagctggtg gtggtcaagg aggtggagct ggtggaggat atggtgcagg tggagagcat
1201 ggaggtggag ctggtggtgg tcaaggaggt ggagctggtg gaggatatgt gcaggtgga
1261 gagcatggag gtggagctgg tggtggtcaa ggaggtggag ctggtggagg atatggtgca
1321 ggtggagagc atggaggtgg agctggtggc ggtcaaggag gtggagctgg tggaggatat
1381 ggtgcaggtg gagagcatgg tggtggaggt ggtggtggtc aaggaggtgg agctggtgga
1441 ggatatgctg cagtaggaga gcatggtggt ggatatgggg gtggtcaagg aggtggagat
1501 ggtggagggt atggtactgg tggagagcat ggtgggggat atgggggtgg ccaaggaggt
1561 ggagctggtg gagggtatgg gactggtgga gagcatggtg gtggttatgg aggaggtcaa
1621 ggaggtggag gaggctatgg tgctggtgga gatcatggtg ctgctgggta tggaggtggt
1681 gaaggaggtg gaggtgggag tggaggaggt tatggagatg gaggagcaca tggaggtgga
1741 tatggtggcg gcgctggtgg aggaggtggg tatggagcag gtggagcaca tggtggtggt
1801 tatggaggag gtggtggaat tggcggggc cacggtggca acgttcccta agaggttctc
1861 cacaaagcac aacagctatc ctcgaggcgc ttttggaata agtatggtgt taataacacg
1921 accat
```

SEQ ID No. 5 Amino acid sequence of Glycine-rich cell wall structural protein 1.0 precursor (GRP 1.0).

```
  1 matskvllsn vlfvfvcfgi csaartlltl edrvnlhvgt vvggyggggg sgggggaav
 61 elggggygeg agggegagag ygaaggghgg gggnggggg gadgggyggg agkgggegyg
121 ggganggyg ggggsggggg ggaggagsgy gggegsgagg gyggangggg ggnggggggg
181 sggahgggaa gggegagqga gggygggaag gggrgsgggg gggygggar gsgyggggs
241 geggghgggy yp
```

SEQ ID No. 6 DNA sequence encoding Glycine-rich cell wall structural protein 1.0 precursor (GRP 1.0).

```
  1 gtggtatatc aggataaatc cacatcaaca agttgttgaa gagctgctgg aaatttgaaa
 61 gaaaaaagaa aattagttgc agtggtcact gttaagtgtg aacatgcaag atgaatgatt
121 ccgccatcct caacagaaaa acgatatac gttttatcag aaaatggaga ataggtttat
181 aagatggcca tagtgagaaa caagatgaat gtaatgctcg tggttcacag acaaaagaca
241 caccagtggg tcttatagtg cgatttctgt acttgtaccc aacaactcct gcatggtgca
301 gtgggccata ttcaagaaat taaacacact tttgggcccc tccatttctg taatgggcca
361 ggcccattac tatatataca cacgaacttt gcattccgaa agccacactt tgcaatggca
```

```
 421 acttctaaag tacttctcag taacgttctt tttgtgtttg tttgttttgg catttgctct 481 gctgctagaa cactcctcac tctagaggac cgtgtgaact tgcatgttgg tactgttgtt 541 ggtggatatg gtggtggtgg aggaagcggc ggcggaggag gaggcgccgc ggtagagctc 601 ggtggtggtg gatacgggga aggagctgga ggaggtgaag gtgccggtgc tggatatgga 661 gctgcgggtg gtggacacgg tggtggtgga ggaaacggtg gtggcggtgg cggtggtgct 721 gatggaggtg gatacggagg aggggctggt aaaggtggtg gtgaaggata tggcggaggt 781 ggagcaaatg ggggtggtta tggtggtgga ggtggaagtg gaggaggagg aggcggtggt 841 gcaggggggtg ctggtagtgg ctatggggggt ggggaaggga gtggggctgg tggtggatac 901 ggtggagcga atggcggagg aggaggcgga atggtgggg gtggtggagg aggttctggc 961 ggagcacatg gtggtggagc agctggtggt ggtgagggag ctggacaagg agccggtgga 1021 ggatatggtg gtggagcagc tggtggcggt ggtcgtggct ctggggggcgg tggcggtgga 1081 ggctatggtg gtggaggtgc acgtgggagt ggatatggag gtggtggtgg gagtggagaa 1141 ggtggtggcc acggtggtgg atactacccc tgaaatgaat acattacata agaaaatatt 1201 taactagctt cttatggcta tagtaaaata ataagaaaat gtattgctga taaactattt 1261 atgcattata ttcactggta ttaatatata tacatgcaag actctttatg atatttaaat 1321 ggtgtgaatg tctttattaa tcatatacat gcaagactac attgcccgat ttcatgaact 1381 ttcattatga gtttctttct gaccaagtta agaagccgt gatggaaaac atgccaactt 1441 caagaattgt tatacaaagt aaatagaact tatatcaatt agtaaattac tattgtgtaa 1501 tattttaaaa aatagaaaca aaagtacgaa atgaacaaaa agaattttac aagaaattgt 1561 attaaatttg acaatcaata ttaattatac aataaattaa taactattca cttaattatt 1621 tattaaaagt gaattggttg aatatgaaaa tgaagttgca aaatatattt ttcttagtgc 1681 aaataatata actaaaaagg gacattctac tttaaagata taacattctt ttattagcaa 1741 aaacaataca tttataaatg aaacaaatag ttgtctcaat ccatttaaat ctttatgtgt 1801 agaggaagat ct
```

SEQ ID No. 7 amino acid sequence of artificial protein comprising YXXX repeats

```
S R E F Y P K N Y G E L Y P K K Y G E L Y P K K Y
G E S Y H K S Y V E S Y H K S Y V E S Y Q K R Y V
E Y Y R K I Y A E Y Y R K I Y A E C Y L K T Y D E
C Y L K T Y D E W Y L K T Y E T S
```

SEQ ID No. 8 DNA sequence encoding an artificial protein comprising YXXX repeats

```
TCT AGA GAG TTT TAC CCT AAG AAC TAT GGT GAG TTG
TAC CCC AAG AAA TAC GGC GAA TTG TAT CCA AAA AAG
TAT GGA GAA TCT TAC CAT AAG AGT TAC GTT GAG TCC
TAT CAC AAA AGC TAT GTC GAA TCA TAC CAA AAG AGA
TAT GTG GAG TAT TAC CGT AAA ATT TAT GCT GAG TAC
TAC CGC AAG ATC TAT GCC GAG TGT TAC CTT AAG ACT
TAT GAT GAA TGC TAT CTC AAA ACC TAC GAC GAA TGG
TAC CTA AAG ACA TAT GAA ACTAGT
```

SEQ ID No. 9;
Forward primer for amplification of SEQ ID No. 2:

5'AAATTTGCATTGGGGCATTA3'

SEQ ID No. 10.
Reverse primer for amplification of SEQ ID No. 2:

5'AGACTTGGAAGGTGGTGGTG3'

SEQ ID No. 11.
Forward Ribosomal 18S specific PCR primer:

5'AAACGGCTACCACATCCAAG3'

SEQ ID No. 12.
Reverse Ribosomal 18S specific PCR primer:

5'CCCAACCCAAAGTCCAACTA3'

SEQ ID No. 13. Signal peptide from beta-glucosidase from *Pinus contorta*.

MEVSVLMWVLLFYSLLGFQVYTTA

SEQ ID No. 14. Signal peptide from Glycine-rich cell wall structural protein 1.8 precursor (GRP 1.8).

MATIHRLPSL VFLVLLALGV CSARRALLTL

SEQ ID No. 15. Signal peptide from Glycine-rich cell wall structural protein 1.0 precursor (GRP 1.0).

MATSKVLLSN VLFVFVCFGI CSAARTLLTL

SEQ ID No. 16. DNA sequence encoding the Signal peptide from beta-glucosidase from *Pinus contorta*.

5' ATGGAGGTGTCTGTGTTGATGTGGGTACTGCTCTTCTATTCCTTATTA GGTTTTCAAGTGACGACAGCT 3'

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

---

The invention claimed is:

1. A method producing fermentable sugar from a lignocellulosic plant, comprising:
   providing a transgenic plant transformed with an expression cassette encoding a protein and a signal peptide which targets the protein to the cell wall of the transgenic plant, where at least 5% of the total amino acid residues of the protein are tyrosine, lysine, serine, threonine or cysteine; and
   degrading lignocellulosic material of the plant, yielding fermentable sugar.

2. The method of claim 1, wherein degrading the lignocellulosic material comprises contacting the lignocellulosic material with a cellulolytic agent.

3. The method of claim 2, wherein the cellulolytic agent is a cellulolytic enzyme.

4. The method of claim 3, wherein the cellulolytic enzyme is selected from the group consisting of: a cellulase, a hemicellulase, an endoglucanase, a cellulobiohydrolase, a beta-glucosidase, an esterase, a laccase, a peroxidase, and a combination thereof.

5. The method of claim 1, wherein degrading the lignocellulosic material comprises contacting the lignocellulosic material with a peptidolytic agent.

6. The method of claim 5, wherein the peptidolytic agent is a peptidolytic enzyme.

7. The method of claim 5, wherein the peptidolytic agent is an acid.

8. The method of claim 1, further comprising fermenting the fermentable sugar to yield a fermentation product.

9. The method of claim 7, wherein the fermentation product is ethanol.

10. The method of claim 7, wherein the fermentation is performed substantially simultaneously with degrading lignocellulosic material of the plant.

* * * * *

UNITED STATES PATENT AND TRADEMARK OFFICE
CERTIFICATE OF CORRECTION

PATENT NO. : 8,163,976 B2  
APPLICATION NO. : 12/126569  
DATED : April 24, 2012  
INVENTOR(S) : Ming Tien et al.

Page 1 of 1

It is certified that error appears in the above-identified patent and that said Letters Patent is hereby corrected as shown below:

Column 3, line 32: After "is" delete "characterized by";
Column 4, line 30: Delete "lignin-protein bonds";
Column 9, line 23: After "promoter" replace "::" with --:--;
Column 9, line 24: After 2003 insert --.--;
Column 9, line 30: Replace "targets" with --target--;
Column 10, line 25: After "increased" delete "an";
Column 12, line 7: Replace "lippocastanaceae" with --Hippocastanaceae--;
Column 14, line 50: After "Wis." delete ")";
Column 14, line 58: Delete "protein rich in";
Column 14, line 62: Delete second occurrence of "protein rich in";
Column 15, line 40: Delete "degree";
Column 22, line 13: Delete second occurrence of "protein rich in";
Column 23, line 6: Replace "µl" with --g/l--;
Column 23, line 12: Replace "µl" with --g/l--;
Column 25, line 26: Delete second occurrence of "protein rich in"; and
Column 26, line 61: After "*tumefaciens*" delete ".".

Signed and Sealed this
Sixth Day of November, 2012

David J. Kappos
*Director of the United States Patent and Trademark Office*

SEQUENCE LISTING

<160> NUMBER OF SEQ ID NOS: 16

<210> SEQ ID NO 1
<211> LENGTH: 315
<212> TYPE: PRT
<213> ORGANISM: Artificial
<220> FEATURE:
<223> OTHER INFORMATION: Fusion protein including the translated leader
      sequence from beta-glucosidase from Pinus contorta and Tyrosine-
      rich hydroxyproline-rich glycoprotein from Petroselinum crispum
      (parsley)

<400> SEQUENCE: 1

```
Met Glu Val Ser Val Leu Met Trp Val Leu Leu Phe Tyr Ser Leu Leu
1               5                   10                  15

Gly Phe Gln Val Thr Thr Ala Arg Leu Asp Arg Asn Asn Phe Pro Ser
            20                  25                  30

Asp Phe Met Phe Gly Thr Ala Ser Ser Ala Tyr Gln Tyr Glu Gly Ala
        35                  40                  45

Val Arg Glu Asp Gly Lys Gly Pro Tyr His Ser Pro Pro Pro Pro Val
    50                  55                  60

Lys Ser Pro Pro Pro Tyr Tyr Tyr Ser Ser Pro Pro Pro Pro Val
65                  70                  75                  80

Lys Ser Pro Pro Pro Tyr Tyr Tyr Thr Ser Pro Pro Pro Pro Val
            85                  90                  95

Lys Ser Pro Pro Pro Tyr Tyr Tyr Thr Ser Pro Pro Pro Met
            100                 105                 110

Lys Ser Pro Pro Pro Tyr Tyr Pro His Pro His Pro His Pro His
            115                 120                 125

Ser Tyr Thr Val Lys Val Val Gly Lys Val Tyr Cys Tyr Arg Cys Tyr
    130                 135                 140

Asp Trp Lys Tyr Pro Ile Lys Ser His Ala Lys Lys His Leu Lys Gly
145                 150                 155                 160

Ala Val Val Glu Val Thr Cys Lys Ala Gly Asp Lys Asp Val Val Thr
                165                 170                 175

Tyr Gly Lys Thr Lys Ile Asn Gly Lys Tyr Ser Ile Thr Val Lys Gly
            180                 185                 190

Phe Glu Tyr Gly Lys Tyr Gly Gly Ala Lys Ala Cys Lys Ala Lys Leu
        195                 200                 205

His Met Ala Pro Lys Asp Ser Lys Cys Asn Ile Pro Thr Asn Leu His
    210                 215                 220

Trp Gly Ile Lys Gly Ala Lys Leu Lys Val Lys Ser Lys Ser Lys Tyr
```

```
                225                 230                 235                 240
            Glu Val Val Leu Ser Ala Lys Pro Phe Ala Tyr Ala Pro Lys Thr Pro
                            245                 250                 255
            Tyr Lys Lys Cys Tyr Lys Pro Val Pro Thr Pro Ala Ala Pro Leu Thr
                        260                 265                 270
            Pro Pro Tyr Tyr Tyr Gln Ser Pro Pro Pro Ser Lys Ser Pro Ala
                    275                 280                 285
            Pro Thr Pro Tyr Tyr Lys Ser Pro Pro Pro Thr Lys Ser Pro
                290                 295                 300
            Ala Pro Thr Pro Tyr Tyr Tyr Lys Ser Pro Arg
            305                 310                 315

<210> SEQ ID NO 2
<211> LENGTH: 948
<212> TYPE: DNA
<213> ORGANISM: Artificial
<220> FEATURE:
<223> OTHER INFORMATION: Fusion protein encoding Tyrosine-rich
      hydroxyproline-rich glycoprotein from Petroselinum crispum
      (parsley) and the leader sequence from beta-glucosidase from Pinus
      contorta

<400> SEQUENCE: 2
atggaggtgt ctgtgttgat gtgggtactg ctcttctatt ccttattagg ttttcaagtg    60
acgacagcta ggctggacag gaacaacttc ccctcagatt tcatgttcgg cacagcctct   120
tcagcgtatc agtatgaagg agcagtccga gaagatggca aggtcctta tcactctcca   180 ccaccaccccg taaaatcccc accaccacct tactactact catcaccacc accaccgta   240 aaatccccac cacctccata ctactacact tcaccaccac caccagtaaa atccccacca   300
ccaccttact actacacctc tccaccacca ccaatgaaat ccccacctcc tccttactac   360
cctcaccctc accctcaccc tcattcatac acagtgaaag ttgtgggaaa ggtctactgt   420
tacagatgct atgactggaa gtacccaatc aagtcccatg caaagaaaca cctcaaaggt   480
gcggttgttg aggtgacatg caaggcagga gacaaagatg tagtgacata tggtaaaaca   540
aagatcaatg gtaaatatag catcacagtt aaaggatttg agtatggaaa atatggtgga   600
gctaaggcat gcaaagctaa gcttcatatg gcaccaaagg attctaaatg taacatacca   660
acaaatttgc attggggcat taagggtgca aaactaaaag tgaaatcaaa gagcaaatat   720
gaagttgttt tgtctgccaa acctttgct tatgctccca aaactcctta caagaagtgt   780
tataagcctg tgccaacacc agcagctcct ttgacaccac ttactatta tcagtctcca   840 ccaccacctt ccaagtctcc ggcaccaact ccttactact ataagtctcc tccaccgcct   900
acgaaatctc cggcgccgac tccttattac tataagtccc cacgatga              948

<210> SEQ ID NO 3
<211> LENGTH: 465
<212> TYPE: PRT
<213> ORGANISM: Phaseolus vulgaris

<400> SEQUENCE: 3

Met Ala Thr Ile His Arg Leu Pro Ser Leu Val Phe Leu Val Leu Leu
1               5                   10                  15

Ala Leu Gly Val Cys Ser Ala Arg Arg Ala Leu Leu Thr Leu Asp Ala
                20                  25                  30

Gly Tyr Gly Leu Gly His Gly Thr Gly Gly Tyr Gly Gly Ala Ala
            35                  40                  45

Gly Ser Tyr Gly Gly Gly Gly Gly Gly Ser Gly Gly Gly Gly Gly
```

-continued

```
            50                  55                  60
Tyr Ala Gly Glu His Gly Val Val Gly Tyr Gly Gly Ser Gly Gly
 65                  70                  75                  80

Gly Gln Gly Gly Gly Val Gly Tyr Gly Gly Asp Gln Gly Ala Gly Tyr
                 85                  90                  95

Gly Gly Gly Gly Gly Ser Gly Gly Gly Gly Val Ala Tyr Gly Gly
                100                 105                 110

Gly Gly Glu Arg Gly Gly Tyr Gly Gly Gln Gly Gly Gly Ala Gly
                115                 120                 125

Gly Gly Tyr Gly Ala Gly Gly Glu His Gly Ile Gly Tyr Gly Gly Gly
                130                 135                 140

Gly Gly Ser Gly Ala Gly Gly Gly Gly Tyr Asn Ala Gly Gly Ala
145                 150                 155                 160

Gln Gly Gly Gly Tyr Gly Thr Gly Gly Gly Ala Gly Gly Gly Gly
                165                 170                 175

Gly Gly Gly Asp His Gly Gly Tyr Gly Gly Gly Gln Gly Ala Gly
                180                 185                 190

Gly Gly Ala Gly Gly Tyr Gly Gly Gly Glu His Gly Gly Gly
                195                 200                 205

Gly Gly Gly Gly Gln Gly Gly Gly Ala Gly Gly Tyr Gly Ala Gly
                210                 215                 220

Gly Glu His Gly Gly Gly Ala Gly Gly Gly Gln Gly Gly Gly Ala Gly
225                 230                 235                 240

Gly Gly Tyr Gly Ala Gly Gly Glu His Gly Gly Gly Ala Gly Gly
                245                 250                 255

Gln Gly Gly Gly Ala Gly Gly Gly Tyr Gly Ala Gly Gly Glu His Gly
                260                 265                 270

Gly Gly Ala Gly Gly Gly Gln Gly Gly Gly Ala Gly Gly Gly Tyr Gly
                275                 280                 285

Ala Gly Gly Glu His Gly Gly Gly Ala Gly Gly Gly Gln Gly Gly Gly
290                 295                 300

Ala Gly Gly Gly Tyr Gly Ala Gly Gly Glu His Gly Gly Gly Gly
305                 310                 315                 320

Gly Gly Gln Gly Gly Gly Ala Gly Gly Gly Tyr Ala Ala Val Gly Glu
                325                 330                 335

His Gly Gly Gly Tyr Gly Gly Gly Gln Gly Gly Gly Asp Gly Gly
                340                 345                 350

Tyr Gly Thr Gly Gly Glu His Gly Gly Gly Tyr Gly Gly Gly Gln Gly
                355                 360                 365

Gly Gly Ala Gly Gly Gly Tyr Gly Thr Gly Gly Glu His Gly Gly Gly
                370                 375                 380

Tyr Gly Gly Gly Gln Gly Gly Gly Gly Tyr Gly Ala Gly Gly Asp
385                 390                 395                 400

His Gly Ala Ala Gly Tyr Gly Gly Gly Glu Gly Gly Gly Gly Ser
                405                 410                 415

Gly Gly Gly Tyr Gly Asp Gly Gly Ala His Gly Gly Gly Tyr Gly Gly
                420                 425                 430

Gly Ala Gly Gly Gly Gly Gly Tyr Gly Ala Gly Gly Ala His Gly Gly
                435                 440                 445

Gly Tyr Gly Gly Gly Gly Gly Ile Gly Gly Gly His Gly Gly Asn Val
                450                 455                 460

Pro
465
```

<210> SEQ ID NO 4
<211> LENGTH: 1925
<212> TYPE: DNA
<213> ORGANISM: Phaseolus vulgaris

<400> SEQUENCE: 4

```
ttaacaaatt tataaaaaag aggtatgttt gcagttgcac ccgatgatag tggtggcaat    60
aagaaaaaaa agggaagaca gaaggaagaa gaagattgag aaagtaaaat gcagtgcaaa   120
atggtggtga gtgggaggta gaaaagaggg ataggtaggt atgaaaaaga aagaaaaaa    180
gcgtaggttt gttggagtag ctagtgtatt tgtatgggta ctgcatgctc cgttggatgt   240
ggaagacagc agaagcacac aatgaagctc cagtatgagt ggtttcagtg tatctttgta   300
tgttaacata atgggccaca ctgtggggca tccaactttc atatccatga gcttcaacca   360
ctctttgctc tcaacgagcc ttcccaatcc ctataaatac ccttcaagtc tcctcacttc   420
aaaaccaacc tatttcagct tcacttcact ctcatggcta ctattcacag gcttcccagt   480
ctagttttct tagtactatt ggctctaggt gtatgttctg ctagaagggc ccttctcacc   540
cttgatgctg gatatggttt aggtcatggc actggtggtg gttatggtgg tgctgctgga   600
agttatggag gtggtggagg tggcggctcg ggtggtggcg gtggatatgc tggggagcat   660
ggagttgttg gtatggagg  tggtagtggc ggaggtcaag gtgggggagt aggatatggt   720
ggtgatcaag gagctggata tggtggtggt ggtggaagtg gtggtggtgg tggtgtggct   780
tacggtggtg gggagagcg  tggtggttat ggtggaggtc aaggaggtgg agctggaggg   840
ggatatggag ctggtggaga acatggcatt gggtatggag gaggtggcgg aagtggtgct   900
ggtggtggag gtgggtataa tgctggagga gcacagggtg gtggatatgg tactggtgga   960
ggagctggtg gcgtggtgg  tggaggagga gatcacggtg gtggttacgg gggtggtcaa  1020
ggagctggag gtggagcagg tggagggtat ggtggtggtg gagagcatgg aggtggaggt  1080
ggtggtggtc aaggaggtgg agctggtgga ggatatggtg caggtggaga gcatggaggt  1140
ggagctggtg gtggtcaagg aggtggagct ggtggaggat atggtgcagg tggagagcat  1200
ggaggtggag ctggtggtgg tcaaggaggt ggagctggtg gaggatatgg tgcaggtgga  1260
gagcatggag gtggagctgg tggtggtcaa ggaggtggag ctggtggagg atatggtgca  1320
ggtggagagc atggaggtgg agctggtggc ggtcaaggag gtggagctgg tggaggatat  1380
ggtgcaggtg gagagcatgg tggtggaggt ggtggtggtc aaggaggtgg agctggtgga  1440
ggatatgctg cagtaggaga gcatggtggt ggatatgggg gtggtcaagg aggtggagat  1500
ggtggagggt atggtactgg tggagagcat ggtgggggat atggggggtgg ccaaggaggt  1560
ggagctggtg gagggtatgg gactggtgga gagcatggtg gtggttatgg aggaggtcaa  1620
ggaggtggag gaggctatgg tgctggtgga gatcatggtg ctgctgggta tggaggtggt  1680
gaaggaggtg gaggtgggag tggaggaggt tatggagatg gaggagcaca tggaggtgga  1740
tatggtggcg gcgctggtgg aggaggtggg tatggagcag gtggagcaca tggtggtggt  1800
tatggaggag gtggtggaat tggcggggc  acggtggca  acgttcccta agaggttctc  1860
cacaaagcac aacagctatc ctcgaggcgc ttttggaata agtatggtgt taataacacg  1920
accat                                                              1925
```

<210> SEQ ID NO 5
<211> LENGTH: 252
<212> TYPE: PRT
<213> ORGANISM: Phaseolus vulgaris

<400> SEQUENCE: 5

```
Met Ala Thr Ser Lys Val Leu Leu Ser Asn Val Leu Phe Val Phe Val
1               5                   10                  15
Cys Phe Gly Ile Cys Ser Ala Ala Arg Thr Leu Leu Thr Leu Glu Asp
            20                  25                  30
Arg Val Asn Leu His Val Gly Thr Val Val Gly Gly Tyr Gly Gly Gly
        35                  40                  45
Gly Gly Ser Gly Gly Gly Gly Gly Ala Ala Val Glu Leu Gly Gly
    50                  55                  60
Gly Gly Tyr Gly Glu Gly Ala Gly Gly Glu Gly Ala Gly Ala Gly
65                  70                  75                  80
Tyr Gly Ala Ala Gly Gly His Gly Gly Gly Gly Asn Gly Gly
                85                  90                  95
Gly Gly Gly Gly Gly Ala Asp Gly Gly Gly Tyr Gly Gly Ala Gly
            100                 105                 110
Lys Gly Gly Gly Glu Gly Tyr Gly Gly Gly Ala Asn Gly Gly
            115                 120                 125
Tyr Gly Gly Gly Gly Ser Gly Gly Gly Gly Gly Gly Ala Gly
    130                 135                 140
Gly Ala Gly Ser Gly Tyr Gly Gly Gly Glu Gly Ser Gly Ala Gly Gly
145                 150                 155                 160
Gly Tyr Gly Gly Ala Asn Gly Gly Gly Gly Gly Asn Gly Gly
                165                 170                 175
Gly Gly Gly Gly Ser Gly Gly Ala His Gly Gly Gly Ala Ala Gly Gly
            180                 185                 190
Gly Glu Gly Ala Gly Gln Gly Ala Gly Gly Tyr Gly Gly Ala
        195                 200                 205
Ala Gly Gly Gly Gly Arg Gly Ser Gly Gly Gly Gly Gly Gly Tyr
    210                 215                 220
Gly Gly Gly Gly Ala Arg Gly Ser Gly Tyr Gly Gly Gly Gly Gly Ser
225                 230                 235                 240
Gly Glu Gly Gly Gly His Gly Gly Gly Tyr Tyr Pro
                245                 250
```

<210> SEQ ID NO 6
<211> LENGTH: 1812
<212> TYPE: DNA
<213> ORGANISM: Phaseolus vulgaris

<400> SEQUENCE: 6

```
gtggtatatc aggataaatc cacatcaaca agttgttgaa gagctgctgg aaatttgaaa      60
gaaaaagaa aattagttgc agtggtcact gttaagtgtg aacatgcaag atgaatgatt     120
ccgccatcct caacagaaaa acggatatac gttttatcag aaaatggaga ataggtttat    180
aagatggcca tagtgagaaa caagatgaat gtaatgctcg tggttcacag acaaaagaca    240
caccagtggg tcttatagtg cgatttctgt acttgtaccc aacaactcct gcatggtgca    300
gtgggccata ttcaagaaat taaacacact tttgggcccc tccatttctg taatgggcca    360
ggcccattac tatatataca cacgaacttt gcattccgaa agccacactt tgcaatggca    420
acttctaaag tacttctcag taacgttctt tttgtgtttg tttgttttgg catttgctct    480
gctgctagaa cactcctcac tctagaggac cgtgtgaact tgcatgttgg tactgttgtt    540
ggtggatatg gtggtggtgg aggaagcggc ggcggaggag gaggcgccgc ggtagagctc    600
ggtggtggtg gatacgggga aggagctgga ggaggtgaag gtgccggtgc tggatatgga    660
```

-continued

```
gctgcgggtg gtggacacgg tggtggtgga ggaaacggtg gtggcggtgg cggtggtgct    720
gatggaggtg gatacggagg aggggctggt aaaggtggtg gtgaaggata tggcggaggt    780
ggagcaaatg ggggtggtta tggtggtgga ggtggaagtg gaggaggagg aggcggtggt    840
gcagggggtg ctggtagtgg ctatgggggt ggggaaggga gtggggctgg tggtggatac    900
ggtggagcga atggcggagg aggaggcgga atggtgggg gtggtggagg aggttctggc    960
ggagcacatg gtggtggagc agctggtggt ggtgagggag ctggacaagg agccggtgga   1020
ggatatggtg gtggagcagc tggtggcggt ggtcgtggct ctgggggcgg tggcggtgga   1080
ggctatggtg gtggaggtgc acgtgggagt ggatatggag gtggtggtgg gagtggagaa   1140
ggtggtggcc acggtggtgg atactacccc tgaaatgaat acattacata gaaaatatt   1200
taactagctt cttatggcta tagtaaaata ataagaaaat gtattgctga taaactattt   1260
atgcattata ttcactggta ttaatatata tacatgcaag actctttatg atatttaaat   1320
ggtgtgaatc tctttattaa tcatatacat gcaagactac attgcccgat ttcatgaact   1380
ttcattatga gtttctttct gaccaagtta agaagccgt gatggaaaac atgccaactt   1440
caagaattgt tatacaaagt aaatagaact tatatcaatt agtaaattac tattgtgtaa   1500
tattttaaaa aatagaaaca aaagtacgaa atgaacaaaa agaatttac aagaaattgt   1560
attaaatttg acaatcaata ttaattatac aataaattaa taactattca cttaattatt   1620
tattaaagt gaattggttg aatatgaaaa tgaagttgca aaatatattt ttcttagtgc    1680
aaataatata actaaaaagg gacattctac tttaaagata taacattctt ttattagcaa   1740
aaacaataca tttataaatg aaacaaatag ttgtctcaat ccatttaaat ctttatgtgt   1800
agaggaagat ct                                                      1812
```

```
<210> SEQ ID NO 7
<211> LENGTH: 92
<212> TYPE: PRT
<213> ORGANISM: Artificial
<220> FEATURE:
<223> OTHER INFORMATION: Artificial protein comprising YXXX repeats

<400> SEQUENCE: 7

Ser Arg Glu Phe Tyr Pro Lys Asn Tyr Gly Glu Leu Tyr Pro Lys Lys
1               5                   10                  15

Tyr Gly Glu Leu Tyr Pro Lys Lys Tyr Gly Glu Ser Tyr His Lys Ser
            20                  25                  30

Tyr Val Glu Ser Tyr His Lys Ser Tyr Val Glu Ser Tyr Gln Lys Arg
        35                  40                  45

Tyr Val Glu Tyr Tyr Arg Lys Ile Tyr Ala Glu Tyr Tyr Arg Lys Ile
    50                  55                  60

Tyr Ala Glu Cys Tyr Leu Lys Thr Tyr Asp Glu Cys Tyr Leu Lys Thr
65                  70                  75                  80

Tyr Asp Glu Trp Tyr Leu Lys Thr Tyr Glu Thr Ser
                85                  90
```

```
<210> SEQ ID NO 8
<211> LENGTH: 276
<212> TYPE: DNA
<213> ORGANISM: Artificial
<220> FEATURE:
<223> OTHER INFORMATION: DNA sequence encoding an artificial protein
      comprising YXXX repeats

<400> SEQUENCE: 8
tctagagagt tttaccctaa gaactatggt gagttgtacc ccaagaaata cggcgaattg    60
```

```
tatccaaaaa agtatggaga atcttaccat aagagttacg ttgagtccta tcacaaaagc    120
tatgtcgaat cataccaaaa gagatatgtg gagtattacc gtaaaattta tgctgagtac    180
taccgcaaga tctatgccga gtgttacctt aagacttatg atgaatgcta tctcaaaacc    240
tacgacgaat ggtacctaaa gacatatgaa actagt                              276
```

<210> SEQ ID NO 9
<211> LENGTH: 20
<212> TYPE: DNA
<213> ORGANISM: Artificial
<220> FEATURE:
<223> OTHER INFORMATION: Forward primer for amplification of SEQ ID NO 2

<400> SEQUENCE: 9

```
aaatttgcat tggggcatta                                                 20
```

<210> SEQ ID NO 10
<211> LENGTH: 20
<212> TYPE: DNA
<213> ORGANISM: Artificial
<220> FEATURE:
<223> OTHER INFORMATION: Reverse primer for amplification of SEQ ID NO 2

<400> SEQUENCE: 10

```
agacttggaa ggtggtggtg                                                 20
```

<210> SEQ ID NO 11
<211> LENGTH: 20
<212> TYPE: DNA
<213> ORGANISM: Artificial
<220> FEATURE:
<223> OTHER INFORMATION: Forward Ribosomal 18S specific PCR primer

<400> SEQUENCE: 11

```
aaacggctac cacatccaag                                                 20
```

<210> SEQ ID NO 12
<211> LENGTH: 20
<212> TYPE: DNA
<213> ORGANISM: Artificial
<220> FEATURE:
<223> OTHER INFORMATION: Reverse Ribosomal 18S specific PCR primer

<400> SEQUENCE: 12

```
cccaacccaa agtccaacta                                                 20
```

<210> SEQ ID NO 13
<211> LENGTH: 23
<212> TYPE: PRT
<213> ORGANISM: Pinus contorta

<400> SEQUENCE: 13

Met Glu Val Ser Val Leu Met Trp Val Leu Leu Phe Tyr Ser Leu Leu
1               5                   10                  15

Gly Phe Gln Val Thr Thr Ala
            20

<210> SEQ ID NO 14
<211> LENGTH: 30
<212> TYPE: PRT
<213> ORGANISM: Phaseolus vulgaris

<400> SEQUENCE: 14

Met Ala Thr Ile His Arg Leu Pro Ser Leu Val Phe Leu Val Leu Leu

-continued

```
                1               5              10              15

Ala Leu Gly Val Cys Ser Ala Arg Arg Ala Leu Leu Thr Leu
                    20              25              30

<210> SEQ ID NO 15
<211> LENGTH: 30
<212> TYPE: PRT
<213> ORGANISM: Phaseolus vulgaris

<400> SEQUENCE: 15

Met Ala Thr Ser Lys Val Leu Leu Ser Asn Val Leu Phe Val Phe Val
1               5              10              15

Cys Phe Gly Ile Cys Ser Ala Ala Arg Thr Leu Leu Thr Leu
                    20              25              30

<210> SEQ ID NO 16
<211> LENGTH: 69
<212> TYPE: DNA
<213> ORGANISM: Pinus contorta

<400> SEQUENCE: 16
atggaggtgt ctgtgttgat gtgggtactg ctcttctatt ccttattagg ttttcaagtg    60
acgacagct                                                            69
```